(12) United States Patent
Puscasu et al.

(10) Patent No.: US 7,973,696 B2
(45) Date of Patent: Jul. 5, 2011

(54) THIN FILM EMITTER-ABSORBER APPARATUS AND METHODS

(75) Inventors: Irina Puscasu, Somerville, MA (US); Edward A. Johnson, Bedford, MA (US)

(73) Assignee: Nomadics, Inc., Stillwater, OK (US)

( * ) Notice: Subject to any disclaimer, the term of this patent is extended or adjusted under 35 U.S.C. 154(b) by 724 days.

(21) Appl. No.: 11/638,042

(22) Filed: Dec. 12, 2006

(65) Prior Publication Data

US 2007/0171120 A1      Jul. 26, 2007

Related U.S. Application Data

(60) Provisional application No. 60/749,468, filed on Dec. 12, 2005.

(51) Int. Cl.
  *H01Q 17/00* (2006.01)
  *H01Q 15/14* (2006.01)
  *H04K 3/00* (2006.01)
  *G01S 7/02* (2006.01)
  *G01S 13/00* (2006.01)

(52) U.S. Cl. .......... 342/4; 342/1; 342/5; 342/13; 342/52; 342/53; 342/175

(58) Field of Classification Search ........... 342/1–20, 342/52–54, 175, 187; 257/499, 528, 532–535, 257/595, 598; 438/104; 428/544, 615, 621, 428/624–627; 359/237, 238, 290, 291–295; 156/229; 361/271, 301.1, 303, 306.1–310, 361/328–330, 500, 523, 524
See application file for complete search history.

(56) References Cited

U.S. PATENT DOCUMENTS

| 2,992,425 | A | * | 7/1961 | Pratt | 342/1 |
| 3,139,568 | A | * | 6/1964 | Ishikawa et al. | 361/524 |
| 3,284,685 | A | * | 11/1966 | Rieth | 361/303 |
| 3,540,047 | A | * | 11/1970 | Walser et al. | 342/1 |
| 3,733,606 | A | * | 5/1973 | Johansson | 342/3 |
| 3,887,920 | A | * | 6/1975 | Wright et al. | 342/1 |

(Continued)

FOREIGN PATENT DOCUMENTS

JP     2003-163487     6/2003

(Continued)

OTHER PUBLICATIONS

International Search Report (PCT/US06/47450); Date of Mailing: Mar. 19, 2008; 1 page.

(Continued)

*Primary Examiner* — Bernarr E Gregory
(74) *Attorney, Agent, or Firm* — Foley & Lardner LLP; Matthew L. Fenselau

(57) ABSTRACT

Methods and apparatus for providing a tunable absorption-emission band in a wavelength selective device are disclosed. A device for selectively absorbing incident electromagnetic radiation includes an electrically conductive surface layer including an arrangement of multiple surface elements. The surface layer is disposed at a nonzero height above a continuous electrically conductive layer. An electrically isolating intermediate layer defines a first surface that is in communication with the electrically conductive surface layer. The continuous electrically conductive backing layer is provided in communication with a second surface of the electrically isolating intermediate layer. When combined with an infrared source, the wavelength selective device emits infrared radiation in at least one narrow band determined by a resonance of the device. In some embodiments, the device includes a control feature that allows the resonance to be selectively modified. The device has broad applications including gas detection devices and infrared imaging.

42 Claims, 16 Drawing Sheets

U.S. PATENT DOCUMENTS

| | | | |
|---|---|---|---|
| 3,955,880 A * | 5/1976 | Lierke | 359/291 |
| 4,456,917 A * | 6/1984 | Sato et al. | 257/598 |
| 4,522,890 A * | 6/1985 | Volkers et al. | 428/624 |
| 4,949,217 A * | 8/1990 | Ngo | 361/328 |
| 5,627,672 A | 5/1997 | Rhoads et al. | |
| 6,072,687 A * | 6/2000 | Naito et al. | 361/303 |
| 6,215,647 B1 * | 4/2001 | Naito et al. | 361/303 |
| 6,266,228 B1 * | 7/2001 | Naito et al. | 361/306.1 |
| 6,266,229 B1 * | 7/2001 | Naito et al. | 361/306.3 |
| 6,292,350 B1 * | 9/2001 | Naito et al. | 361/306.3 |
| 6,323,057 B1 * | 11/2001 | Sone | 438/104 |
| 6,351,369 B1 * | 2/2002 | Kuroda et al. | 361/306.3 |
| 6,407,904 B1 * | 6/2002 | Kuroda et al. | 361/303 |
| 6,430,025 B2 * | 8/2002 | Naito et al. | 361/303 |
| 6,433,993 B1 * | 8/2002 | Hunt et al. | 361/303 |
| 6,441,771 B1 * | 8/2002 | Victora | 342/1 |
| 6,538,596 B1 | 3/2003 | Gilbert | |
| 6,774,866 B2 * | 8/2004 | McKinzie et al. | 343/909 |
| 6,794,729 B2 * | 9/2004 | Mori et al. | 257/532 |
| 6,819,543 B2 * | 11/2004 | Vieweg et al. | 361/306.3 |
| 2002/0088977 A1 * | 7/2002 | Mori et al. | 257/68 |
| 2002/0109095 A1 | 8/2002 | Johnson et al. | |
| 2002/0145792 A1 | 10/2002 | Jacobson et al. | |
| 2003/0124291 A1 | 7/2003 | Ausen et al. | |
| 2004/0126050 A1 | 7/2004 | Claydon et al. | |

FOREIGN PATENT DOCUMENTS

| | | |
|---|---|---|
| WO | WO 00/07411 | 2/2000 |
| WO | WO 2004/093244 | 10/2004 |
| WO | WO 2005/084097 | 2/2005 |

OTHER PUBLICATIONS

Supplementary European Search Report issued in EP application No. 06 84 5312 on Oct. 30, 2009.

* cited by examiner

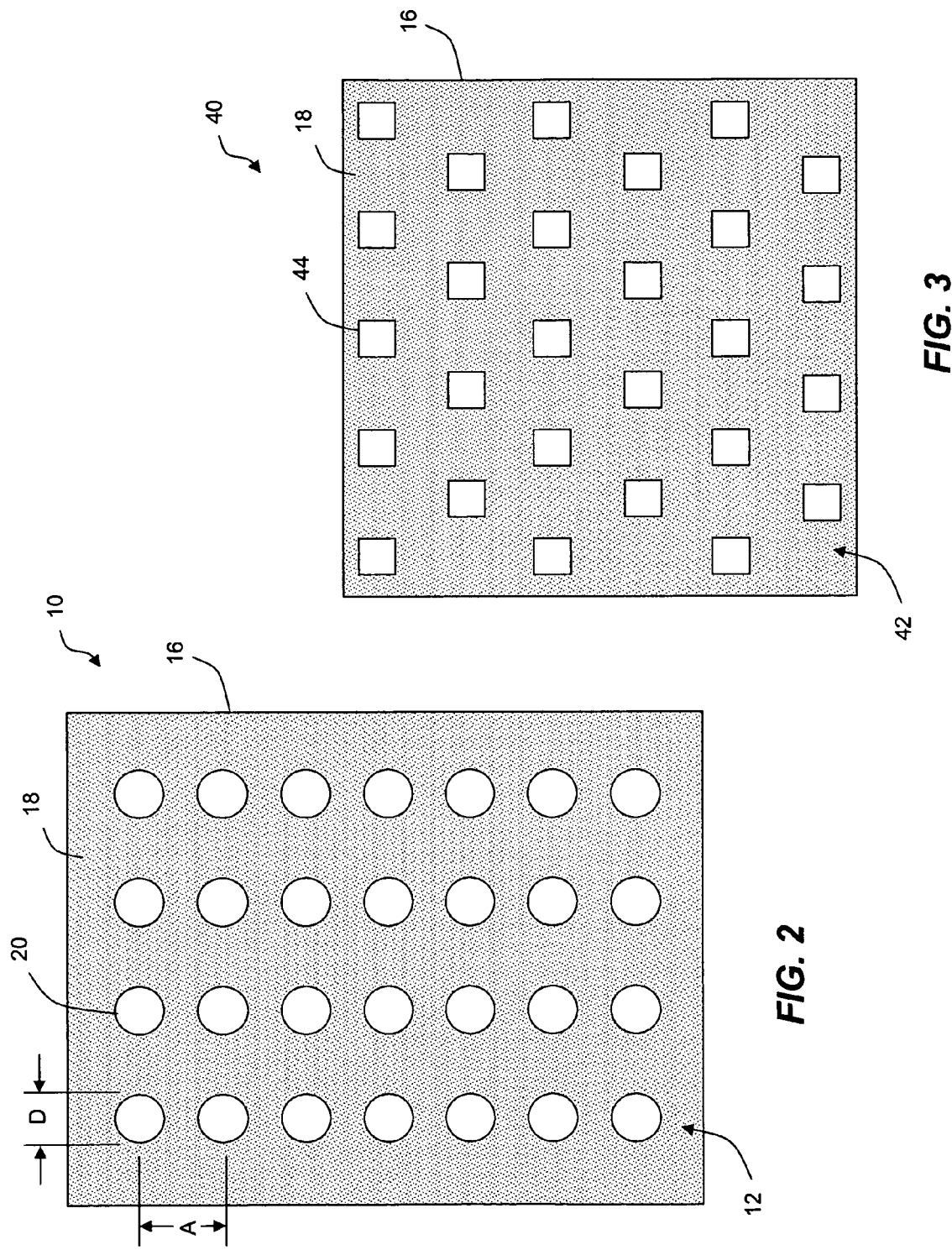

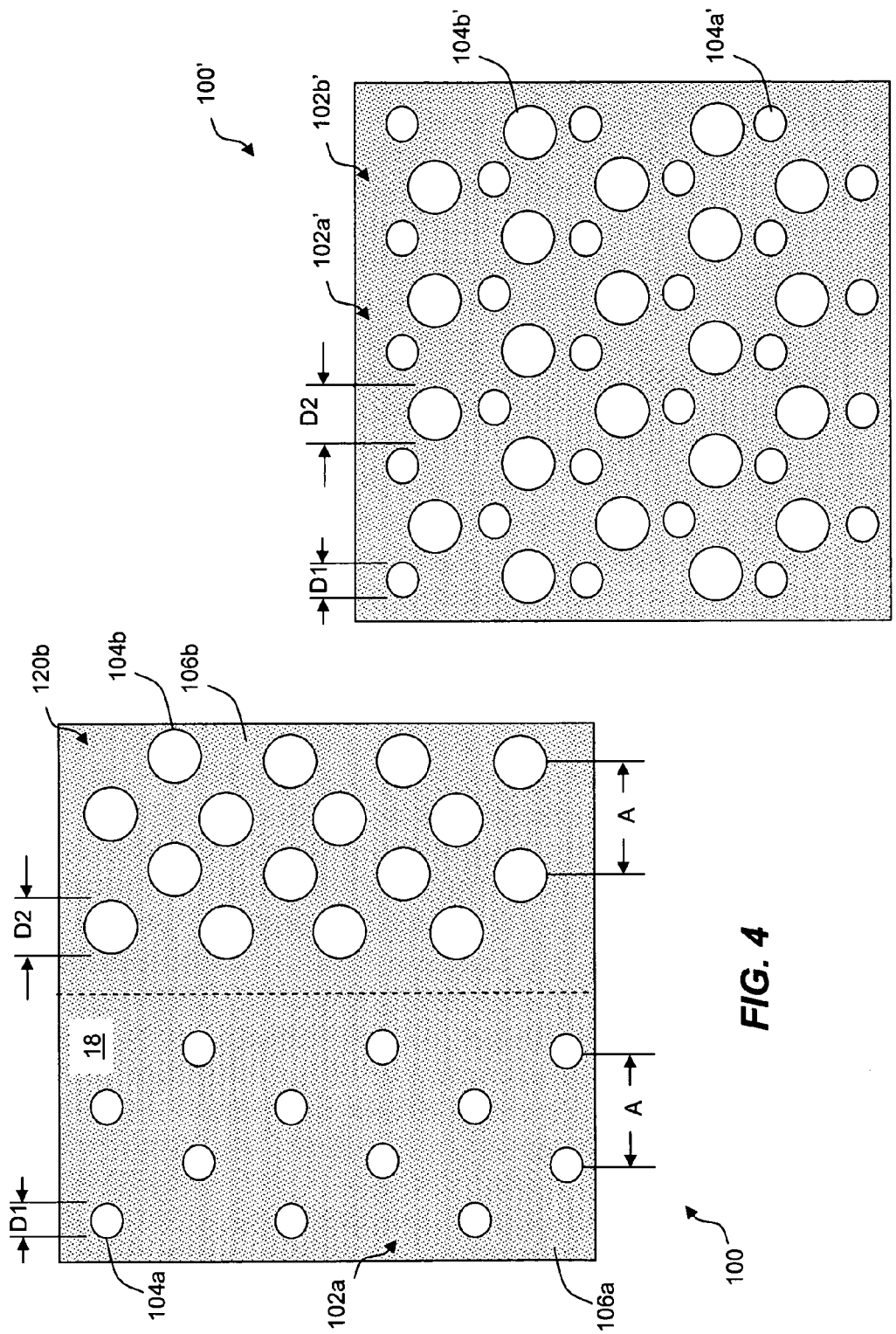

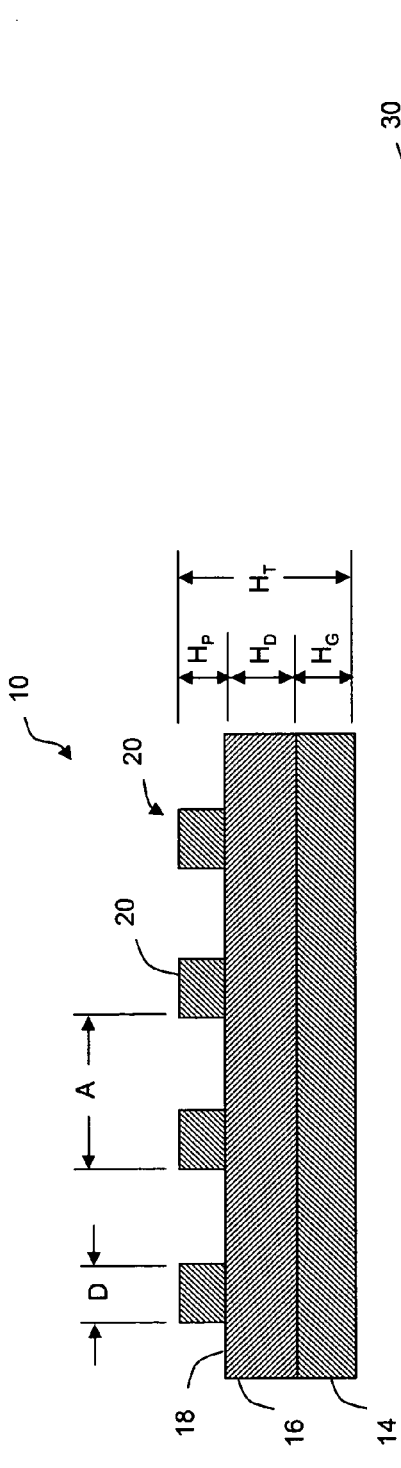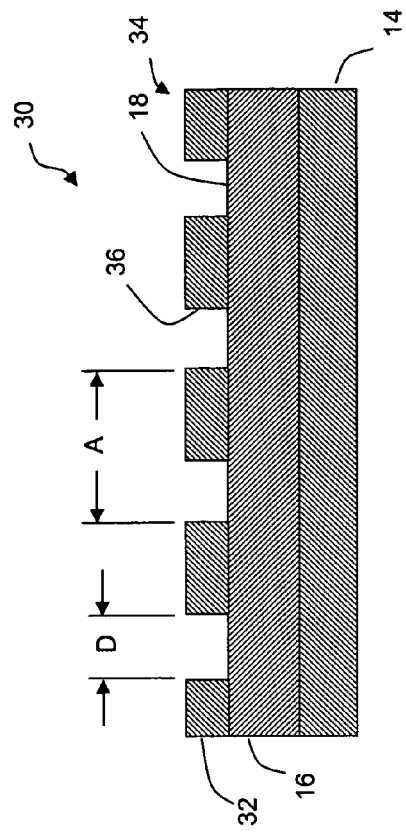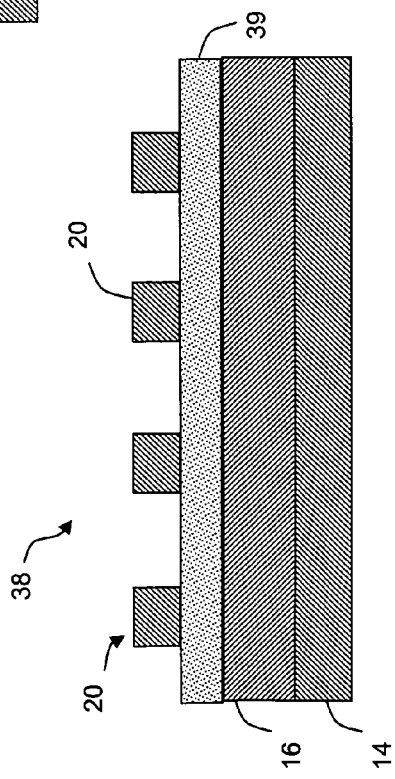

THIN FILM EMITTER-ABSORBER APPARATUS AND METHODS

RELATED APPLICATIONS

This application is claims the benefit of priority under 35 U.S.C. §119 from U.S. Provisional Application Ser. No. 60/749,468, filed on Dec. 12, 2005, the contents of which are incorporated herein by reference in their entirety.

FIELD OF THE INVENTION

The present invention relates generally to reflector and emitter-absorber structures, and more particularly to thin film reflector and emitter-absorber structures formed using multiple conductive elements over a ground plane.

BACKGROUND OF THE INVENTION

Frequency selective surfaces can be provided to selectively reduce or enhance reflections from incident electromagnetic radiation. Such surfaces are often employed in signature management applications to reduce radar returns. These applications are typically employed within the radio frequency portion of the electromagnetic spectrum.

As modern radar systems are often equipped with different and even multiple frequency bands, such signature management surfaces are preferably broad band, reducing reflections over a broad portion of the spectrum. Examples of known frequency selective surfaces providing such a response include one or more than one dielectric layers, which may be disposed above a ground plane. Thickness of the dielectric layers combined with the selected material properties reduce reflected radiation. The thickness of one or more of the layers is a predominant design criteria and is often on the order of one quarter wavelength. Unfortunately, such structures can be complicated and relatively thick, depending upon the selected dielectric materials and wavelength of operation, particularly since multiple layers are often employed.

The use of multiple frequency selective surfaces disposed above a ground plane, for radio frequency applications, is described in U.S. Pat. No. 6,538,596 to Gilbert. The frequency selective surfaces can include conductive materials in a geometric pattern with a spacing of the multiple frequency selective surface layers, which can be closer than a quarter wave. However, Gilbert seems to rely on the multiple frequency selective surfaces providing a virtual continuous quarter wavelength effect. Such a quarter wavelength effect results in a canceling of the fields at the surface of the structure. Thus, although individual layers may be spaced at less than one-quarter wavelength (e.g., $\lambda/12$ or $\lambda/16$), Gilbert relies on macroscopic (far field) superposition of resonances from three of four sheets, such that the resulting structure thickness will be on the order of one-quarter wavelength.

SUMMARY OF THE INVENTION

What is needed is a simple, thin, wavelength selective surface capable of providing a tunable reflection or absorption-emission band. Preferably, the location of the reflection or absorption-emission band as well as its bandwidth can be tuned.

Various embodiments of the present invention provide an apparatus and method for providing a tunable absorption-emission band in a highly reflective wavelength selective surface. An array of surface elements are defined in an electrically conductive layer disposed above a continuous electrically conductive layer, or ground plane.

In a first aspect, the invention relates to a tunable device for selectively coupling electromagnetic radiation. The tunable device includes a first electrically conductive layer having a group of discrete surface elements. The tunable device also includes an electrically insulating intermediate layer defining a first surface in communication with the electrically conductive surface layer and a second, continuous electrically conductive layer in communication with a second surface of the electrically insulating intermediate layer. A terminal is included in electrical communication with at least one of the first electrically conductive layer, the electrically insulating intermediate layer, and the second continuous, electrically conductive layer. The group of discrete surface elements resonantly couples at least a portion of the electromagnetic radiation with respect to the continuous electrically conductive layer.

In another aspect, the invention relates to a tunable infrared (IR) emitter. The tunable IR emitter includes a first electrically conductive layer including a group of discrete surface elements, an electrically insulating intermediate layer defining a first surface in communication with the electrically conductive surface layer, and a second, continuous electrically conductive layer in communication with a second surface of the electrically insulating intermediate layer. The tunable IR device also includes an IR source in thermal communication with at least one of the first electrically conductive layer, the electrically insulating layer and the second, continuous electrically conductive layer. The IR source generates broadband infrared radiation. The group of discrete surface elements electromagnetically couples at least a portion of the broadband infrared radiation to produce a tuned, narrowband IR emission.

In another aspect, the invention relates to controllable wavelength selective device. The controllable device includes a first electrically conductive layer including a group of discrete surface elements, an electrically insulating intermediate layer defining a first surface in communication with the electrically conductive surface layer, and a second, continuous electrically conductive layer in communication with a second surface of the electrically insulating intermediate layer. At least one of the first electrically conductive layer, the electrically insulating intermediate layer, and the second electrically conductive layer provides an externally controllable electrical conductivity.

In yet another aspect, the invention relates to a method of manufacturing a wavelength selective device. The method of manufacturing includes forming a continuous, electrically thin conductive ground layer on a substrate. An electrically thin insulating layer is applied to a top surface of the ground layer. An electrically thin outer conductive layer is formed on the electrically thin insulating layer. The electrically thin outer conductive layer includes a plurality of discrete surface elements.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 shows a top planar view of the wavelength selective surface of FIG. 1.

FIG. 3 shows a top planar view of another embodiment of a wavelength selective surface in accordance with the principles of the present invention having a hexagonal array of electrically conductive square surface elements.

FIG. 4 shows a top planar view of another embodiment of a wavelength selective surface having two resonances.

FIG. 5 shows a top planar view of an alternative embodiment of the dual wavelength device of FIG. 4.

FIG. 7A shows a cross-sectional elevation view of the wavelength selective surface of FIG. 1 taken along A-A.

FIG. 7B shows a cross-sectional elevation view of the wavelength selective surface of FIG. 6 taken along B-B.

FIG. 7C shows a cross-sectional elevation view of an alternative embodiment of a wavelength selective surface having a second intermediate layer.

DETAILED DESCRIPTION OF THE PREFERRED EMBODIMENTS

A description of preferred embodiments of the invention follows.

Figure 1:
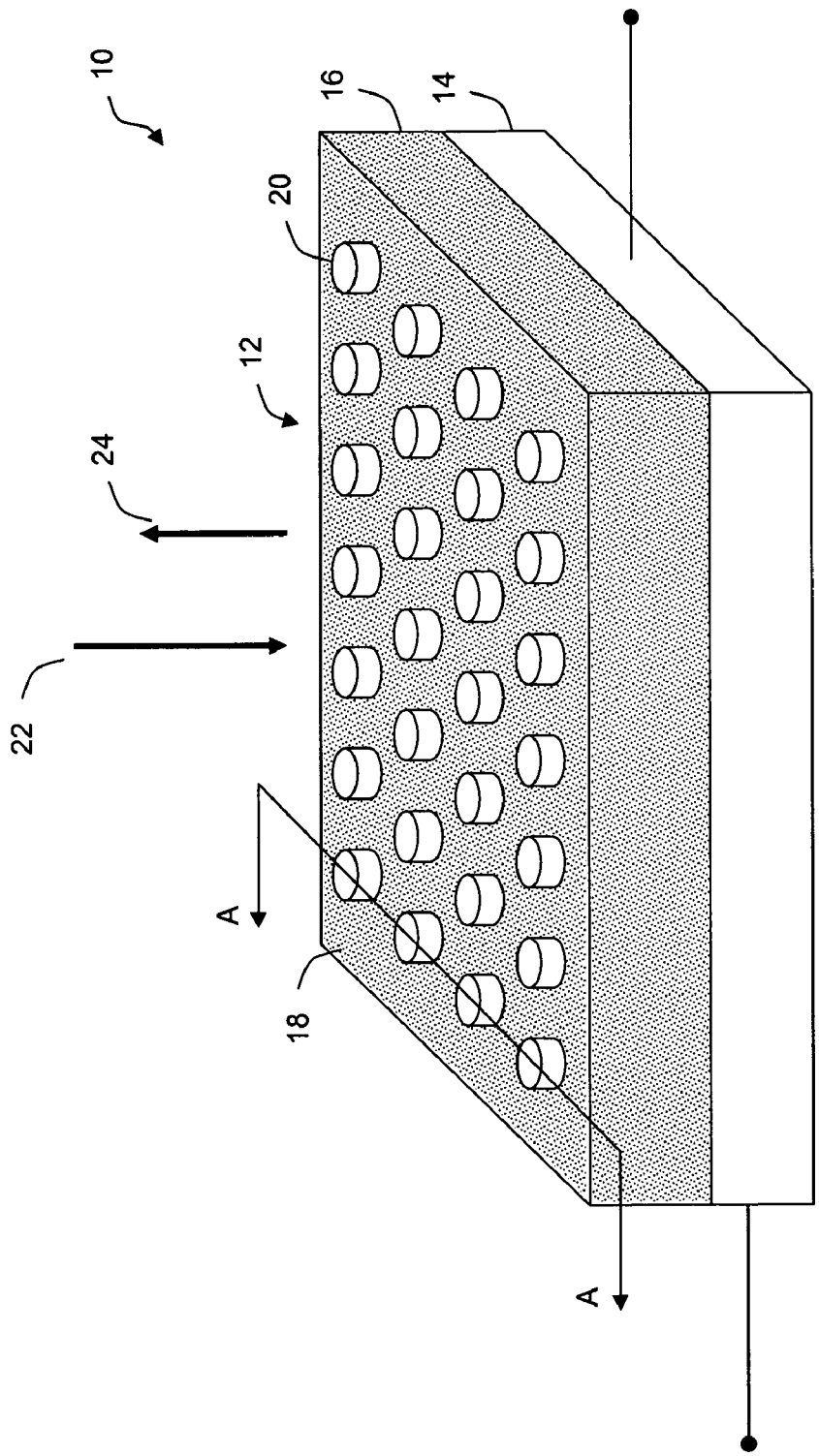
FIG. 1 shows a top perspective view of one embodiment of a wavelength selective surface having a rectangular array of electrically conductive surface elements.

An exemplary embodiment of a wavelength selective surface 10 is shown in FIG. 1. The wavelength selective surface 10 includes at least three distinguishable layers. The first layer is an electrically conductive outer or surface layer 12 including an arrangement of surface elements 20. The surface elements 20 of the outer layer 12 are disposed at a height above an inner layer including a continuous electrically conductive sheet, or ground layer 14. The arrangement of surface elements 20 and ground layer 14 is separated by an intermediate layer 16 disposed therebetween. At least one function of the intermediate layer 16 is to maintain a physical separation between the arrangement of surface elements 20 and the ground layer 14. The intermediate layer 16 also provides electrical isolation between the two electrically conductive layers 12, 14.

In operation, wavelength selective surface 10 is exposed to incident electromagnetic radiation 22. A variable portion of the incident radiation 22 is coupled to the wavelength selective surface 10. The level of coupling depends at least in part upon the wavelength of the incident radiation 22 and a resonant wavelength of the wavelength selective surface 10, as determined by related design parameters. Radiation coupled to the wavelength selective surface 10 can also be referred to as absorbed radiation. At other non-resonant wavelengths, a substantial portion of the incident radiation is reflected 24.

In more detail, the electrically conductive surface layer 12 includes multiple discrete surface features, such as the electrically conductive surface elements 20 arranged in a pattern along a surface 18 of the intermediate layer 16. The discrete nature of the arrangement of surface features 20 requires that individual surface elements 20 are isolated from each other. This also precludes interconnection of two or more individual surface elements 20 by electrically conducting paths. Two or more individual surface elements which are connected electrically form a composite surface element which gives rise to a new resonance.

The electrically conductive surface layer 12 including an arrangement of surface elements 20 is typically flat, having a smallest dimension, height, measured perpendicular to the intermediate layer surface 18. In general, each surface element 20 defines a surface shape and a height or thickness measured perpendicular to the intermediate layer surface 18. In general, the surface shape can be any closed shape, such as closed curves, regular polygons, irregular polygons, star-shapes having three or more legs, and other closed structures bounded by piecewise continuous surfaces including one or more curves and lines. In some embodiments, the surface shapes can include annular features, such as ring shaped patch with an open center region. More generally, the annular features have an outer perimeter defining the outer shape of the patch and an inner perimeter defining the shape of the open inner region of the patch. Each of the outer an inner perimeters can have a similar shape, as in the ring structure, or a different shape. Shapes of the inner and outer perimeters can include any of the closed shapes listed above (e.g., a round patch with a square open center).

The shapes can be selected to provide a resonant response having a preferred polarization. For example, surface features having an elongated shape provide a resonant response that is more pronounced in a polarization that is related to the orientation of the elongated shape. Thus, an array of vertically aligned narrow rectangles produces a response having a vertically aligned linear polarization. In general, preferred polarizations can be linear, elliptical, and circular.

Each of the electrically conductive surface elements 20 is formed with an electrically conductive material. Such conductive materials include ordinary metallic conductors, such as aluminum, copper, gold, silver, platinum, manganese, iron, nickel, tin, lead, and zinc; as well as combinations of one or more metals in the form of a metallic alloy, such as steel, and ceramic conductors such as indium tin oxide and titanium nitride. Alternatively or in addition, conductive materials used in formation of the surface elements 20 include semiconductors. Preferably, the semiconductors are electrically conductive. Exemplary semiconductor materials include: silicon and germanium; compound semiconductors such as silicon carbide, gallium-arsenide and indium-phosphide; and alloys such as silicon-germanium and aluminum-gallium-arsenide. Electrically conductive semiconductors are typically doped with one or more impurities in order to provide good electrical conductivity. Similarly, the ground layer 14 can include one or more electrically conductive materials, such as those described herein.

The intermediate layer 16 can be formed from an electrically insulative material, such as a dielectric providing electrical isolation between the arrangement of surface elements 20 and the ground layer 14. Some examples of dielectric materials include silicon dioxide ($SiO_2$); alumina ($Al_2O_3$); aluminum oxynitride; silicon nitride ($Si_3N_4$). Other exemplary dielectrics include polymers, rubbers, silicone rubbers, cellulose materials, ceramics, glass, and crystals. Dielectric materials also include: semiconductors, such as silicon and germanium; compound semiconductors such as silicon carbide, gallium-arsenide and indium-phosphide; and alloys such as silicon-germanium and aluminum-gallium-arsenide; and combinations thereof. As dielectric materials tend to concentrate an electric field within themselves, an intermediate dielectric layer 16 will do the same, concentrating an induced electric field between each of the surface elements 20 and a proximal region of the ground layer 14. Beneficially, such concentration of the electric-field tends to enhance electromagnetic coupling of the arrangement of surface elements 12 to the ground layer 14.

Dielectric materials can be characterized by parameters indicative of their physical properties, such as the real and imaginary portions of the index of refraction, often referred to as "n" and "k." Although constant values of these parameters n, k can be used to obtain an estimate of the material's performance, these parameters are typically wavelength dependent for physically realizable materials. In some embodiments, the intermediate layer 16 includes a so-called high-k material. Examples of such materials include oxides, which can have k values ranging from 0.001 up to 10.

The arrangement of surface elements 20 can be configured in a preferred arrangement, or array on the intermediate layer surface 18. Referring now to FIG. 2, the wavelength selective surface 10 includes an exemplary array of flattened, electrically conductive surface elements 20. Multiple surface elements 20 are arranged in a square grid along the intermediate layer surface 18. A square grid or matrix arrangement is an example of a regular array, meaning that spacing between adjacent surface elements 20 is substantially uniform. Other examples of regular arrays, or grids include hexagonal grids, triangular grids, oblique grids, centered rectangular grids, and Archimedean grids. In some embodiments, the arrays can be irregular and even random. Each of the individual elements 20 can have substantially the same shape, such as the circular shape shown.

Although flattened elements are shown and described, other shapes are possible. For example, each of the multiple surface elements 20 can have non-flat profile with respect to the intermediate layer surface 18, such as a parallelepiped, a cube, a dome, a pyramid, a trapezoid, or more generally any other shape. One major advantage of the present invention over other prior art surfaces is a relaxation of the fabrication tolerances. The high field region resides underneath each of the multiple surface elements 20, between the surface element 20 and a corresponding region of the ground layer 14.

In more detail, each of the circular elements 20 has a respective diameter D. In the exemplary square grid, each of the circular elements 20 is separated from its four immediately adjacent surface elements 20 by a uniform grid spacing A measured center-to-center. An alternative embodiment of another wavelength selective surface 40 including a hexagonal arrangement, or array of surface elements 42 is shown in FIG. 3. Each of the discrete surface elements includes a square surface element 44 having a side dimension D'. Center-to-center spacing between immediately adjacent elements 44 of the hexagonal array 42 is about A'. For operation in the infrared portion of the electromagnetic spectrum, D will generally be between about 0.5 microns for near infrared and 50 microns for the far infrared and terahertz, understanding that any such limits are not firm and will very depending upon such factors as n, k, and the thickness of layers.

Array spacing A can be as small as desired, as long as the surface elements 20 do not touch each other. Thus, a minimum spacing will depend to some extent on the dimensions of the surface feature 20. Namely, the minimum spacing must be greater than the largest diameter of the surface elements (i.e., A>D). The surface elements can be separated as far as desired, although absorption response suffers from increased grid spacing as the fraction of the total surface covered by surface elements falls below 10%.

In some embodiments, more than one arrangement of uniform-sized features are provided along the same outer surface layer of a wavelength selective surface. Shown in FIG. 4 is a plan view of one such device 100 having two different arrangements of electrically conductive features 102a, 102b (generally 102) disposed along the same surface. The first arrangement 102a includes a triangular array, or grid, of uniform-sized circular patches 104a, each having a diameter $D_1$ and separated from its nearest neighbors by a uniform grid spacing A. Similarly, the second arrangement 102b includes a triangular grid of uniform-sized circular patches 104b, each having a diameter $D_2$ and separated from its nearest neighbors by a uniform grid spacing A. Visible between the circular patches 104a, 104b is an outer surface 18 of the intermediate layer. Each of the arrangements 102a, 102b occupies a respective, non-overlapping region 106a, 106b of the intermediate layer surface 18. Except for there being two different arrangements 102a, 102b on the same surface 18, the device 100 is substantially similar to the other wavelength selective devices described hereinabove. That is, the device 100 also includes a ground plane 14 (not visible in this view) and an intermediate insulating layer 16 disposed between the ground plane 14 and a bottom surface of the circular patches 104a, 104b.

Continuing with this illustrative example, each of the different arrangements 102a, 102b is distinguished from the other by the respective diameters of the different circular patches 104a, 104b (i.e., $D_2 > D_1$). Other design attributes including the shape (i.e., circular), the grid format (i.e., triangular), and the grid spacing of the two arrangements 102a, 102b are the substantially same. Other variations of a multi-resonant device are possible with two or more different surface arrangements that differ from each other according to one or more of: shape; size; grid format; spacing; and choice of materials. Size includes thickness of each of the multiple layers 14, 16, 102 of the device 100. Different materials can also be used in one or more of the regions 106a, 106b. For example, an arrangement of gold circular patches 102a in one region 106a and an arrangement of aluminum circular patches 102b in another region 106b.

In operation, each of the different regions 106a, 106b will respectively contribute to a different resonance from the same wavelength selective device 100. Thus, one device can be configured to selectively provide a resonant response to incident electromagnetic radiation within more than one spectral regions. Such features are beneficial in IR applications in which the device 100 provides resonant emission peaks in more than one IR band. Thus, a first resonant peak can be provided within a 3-5 μm IR band, while a second resonant peak can be simultaneously provided within a 7-14 μm IR band, enabling the same device to be simultaneously visible to IR detectors operating in either of the two IR bands.

In some embodiments, the different arrangements 102a' and 102b' can overlap within at least a portion of the same region. An exemplary embodiment is shown in FIG. 5 having a substantially complete overlap, in which a first arrangement 102a' includes a triangular grid of uniform-sized circular patches 104a' of a first diameter $D_1$, interposed within the same region with a second arrangement 102b' including a triangular grid of uniform-sized circular patches 104b' of a second diameter $D_2$. Each arrangement 102a', 102b' has a grid spacing of A. When exposed to incident electromagnetic radiation, device 100' will produce more than one resonant features, with each resonant feature corresponding to a respective one of the different arrangements 102a', 102b'. As with the previous example, one or more of the parameters including: shape; size; grid format; spacing; and choice of materials can be varied between the different arrangements 102a', 102b'.

In yet other embodiments (not shown), devices similar to those described above in relation to FIG. 4 and FIG. 5 are formed having a complementary surface. Thus, a single device includes two or more different arrangements of through holes formed in an electrically conductive layer above and isolated from a common ground layer. One or more of the through-hole size, shape, grid format, grid spacing, thickness, and materials can be varied to distinguish the two or more different arrangements. Once again, the resulting device exhibits at least one respective resonant feature for each of the two or more different arrangements.

Figure 6:
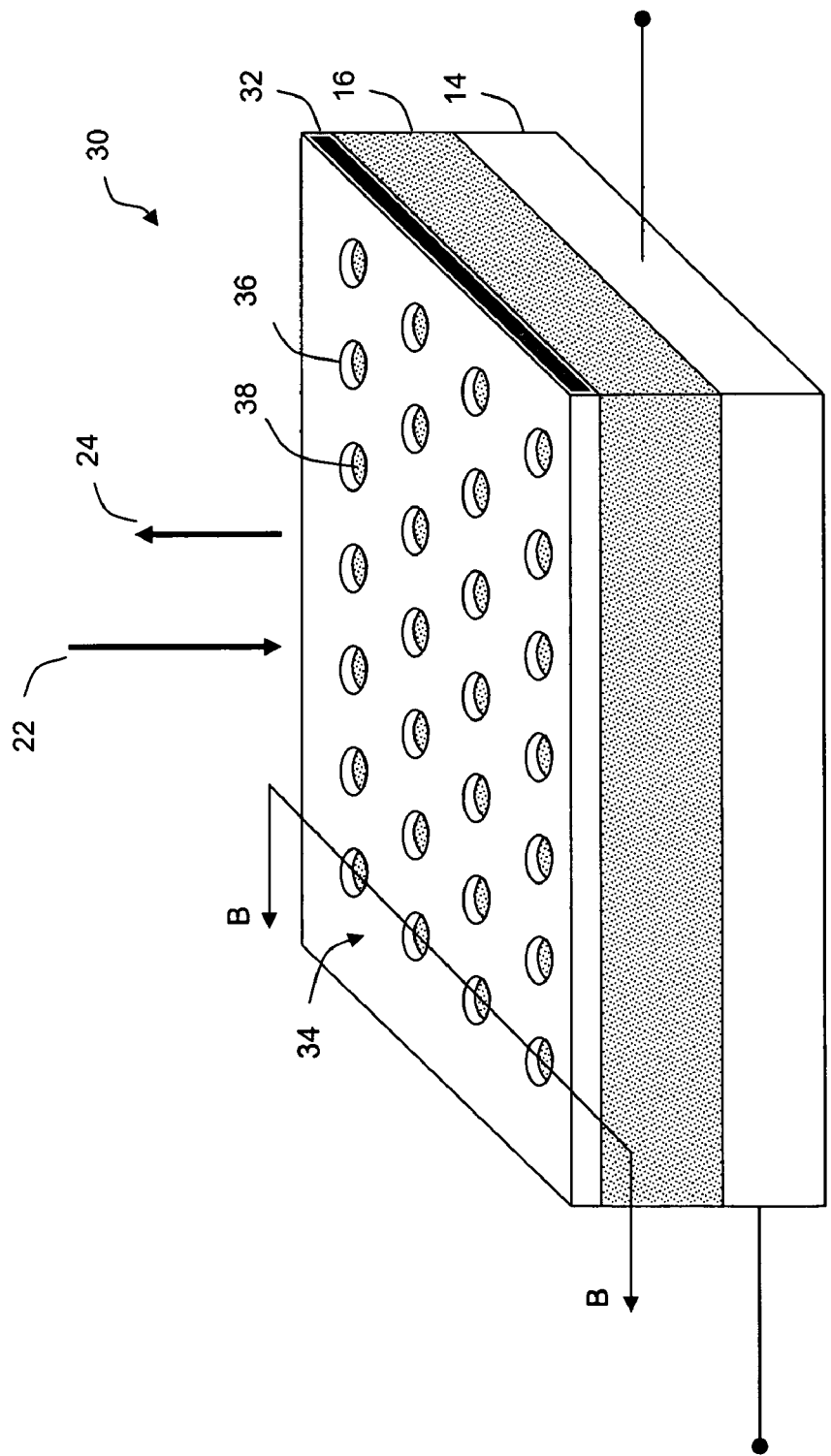
FIG. 6 shows a top perspective view of an alternative embodiment of a wavelength selective surface having apertures defined in an electrically conductive surface layer.

An exemplary embodiment of an alternative family of wavelength selective surfaces 30 is shown in FIG. 6. The alternative wavelength selective surfaces 30 also include an intermediate layer 16 stacked above a ground layer 14; however, an electrically conductive surface 32 layer includes a complementary feature 34. The complementary feature 34 includes the electrically conductive layer 32 defining an arrangement of through apertures, holes, or perforations.

The electrically conductive layer 32 is generally formed having a uniform thickness. The arrangement of through apertures 34 includes multiple individual through apertures 36, each exposing a respective surface region 38 of the intermediate layer 16. Each of the through apertures 36 forms a respective shape bounded by a closed perimeter formed within the conductive layer 32. Shapes of each through aperture 36 include any of the shapes described above in reference to the electrically conductive surface elements 20 (FIG. 1), 44 (FIG. 3).

Additionally, the through apertures 36 can be arranged according to any of the configurations described above in reference to the electrically conductive surface elements 20, 44. This includes a square grid, a rectangular grid, an oblique grid, a centered rectangular grid, a triangular grid, a hexagonal grid, and random grids. Thus, any of the possible arrangements of surface elements 36 and corresponding exposed regions of the intermediate layer surface 18 can be duplicated in a complementary sense in that the surface elements 20 are replaced by through apertures 36 and the exposed regions of the intermediate layer surface 18 are replaced by the electrically conductive layer 32.

A cross-sectional elevation view of the wavelength selective surface 10 is shown in FIG. 7A. The electrically conductive ground layer 14 has a substantially uniform thickness $H_G$. The intermediate layer 16 has a substantially uniform thickness $H_D$, and each of the individual surface elements 20 has a substantially uniform thickness $H_P$. The different layers 12, 14, 16 can be stacked without gaps therebetween, such that a total thickness $H_T$ of the resulting wavelength selective surface 10 is substantially equivalent to the sum of the thicknesses of each of the three individual layers 14, 16, 12 (i.e., $H_T = H_G + H_D + H_P$). A cross-sectional elevation view of the complementary wavelength selective surface 30 is shown in FIG. 7B and including a similar arrangement of the three layers 14, 16, 32.

In some embodiments, the intermediate insulating layer has a non-uniform thickness with respect to the ground layer. For example, the intermediate layer may have a first thickness $H_D$ under each of the discrete conducting surface elements and a different thickness, or height at regions not covered by the surface elements. It is important that a sufficient layer of insulating material be provided under each of the surface elements to maintain a design separation and to provide isolation between the surface elements and the ground layer. In at least one example, the insulating material can be substantially removed at all regions except those immediately underneath the surface elements. In other embodiments, the insulating layer can include variations, such as a taper between surface elements. At least one benefit of the inventive design is a relaxation of design tolerances that results in a simplification of fabrication of the devices.

The thickness chosen for each of the respective layers 12, 32, 16, 14 ($H_P$, $H_D$, $H_G$) can be independently varied for various embodiments of the wavelength selective surfaces 10, 30. For example, the ground plane 14 can be formed relatively thick and rigid to provide a support structure for the intermediate and surface layers 16, 12, 32. Alternatively, the ground plane 14 can be formed as a thin layer, as long as a thin ground plane 14 forms a substantially continuous electrically conducting layer of material providing the continuous ground. Preferably, the round plane 14 is at least as thick as one skin depth within the spectral region of interest. Similarly, in different embodiments of the wavelength selective surfaces 10, 30, the respective surface layer 12, 32 can be formed with a thickness $H_P$ ranging from relatively thin to relatively thick. In a relatively thin embodiment, the surface layer thickness $H_P$ can be a minimum thickness required just to render the intermediate layer surface 18 opaque. Preferably, the surface layer 12, 32 is at least as thick as one skin depth within the spectral region of interest.

Likewise, the intermediate layer thickness $H_D$ can be formed as thin as desired, as long as electrical isolation is maintained between the outer and inner electrically conducting layers 12, 32, 14. The minimum thickness can also be determined to prevent electrical arcing between the isolated conducting layers under the highest anticipated induced electric fields. Alternatively, the intermediate layer thickness $H_D$ can be formed relatively thick. The concept of thickness can be defined relative to an electromagnetic wavelength '$\lambda_c$' of operation, or resonance wavelength. For example, the intermediate layer thickness $H_D$ can be selected between about $0.01\lambda_c$ in a relatively thin embodiment to about $0.5\lambda_c$ in a relatively thick embodiment.

Referring to FIG. 7C, a cross sectional view of a wavelength selective device 38 includes an arrangement of surface features 20 disposed over ground plane 14, with an intermediate insulating layer 16 disposed between the surface features 20 and the ground plane 14. The device 38 also includes a second intermediate layer 39 disposed between a top surface 18 of the insulating layer and a bottom surface of the surface features 20. The second layer 39 is also an insulating material, such that the individual surface features 20 remain discrete and electrically isolated from each other with respect to a non time-varying electrical stimulus. For example, the second intermediate layer 39 can be formed from a dielectric material chosen to have material properties n, k different than the material properties of the first intermediate layer 16. Any dielectric material can be used including any of the dielectric materials described herein. Alternatively or in addition, the second intermediate layer 39 can be formed from a semiconductor material. Any semiconductor can be used, including those semiconductor and semiconductor compounds described herein, provided that the semiconductor includes an electrically insulating mode. More generally, a fourth layer having physical properties described above in relation to the second intermediate layer 39 can be provided between any of the three layers 14, 16, 20 of the device 38.

The wavelength selective surfaces 10, 30 can be formed using standard semiconductor fabrication techniques. Thin devices can be obtained using standard fabrication techniques on a typical semiconductor substrate, followed by a release step, which the thin device is released from the substrate. One such technique is referred to as back-side etching, in which a sacrificial layer is removed underneath the device formed upon the semiconductor substrate. Removal of the sacrificial layer releases a thin-film device from the substrate.

Alternatively or in addition, the wavelength selective surfaces 10, 30 can be formed using thin film techniques including vacuum deposition, chemical vapor deposition, and sputtering. In some embodiments, the conductive surface layer 12, 44 can be formed using printing techniques. The surface features can be formed by providing a continuous electrically conductive surface layer and then removing regions of the surface layer to form the surface features. Regions can be formed using standard physical or chemical etching techniques. Alternatively or in addition, the surface features can be formed by laser ablation, removing selected regions of the conductive material from the surface, or by nano-imprinting or stamping, or other fabrication methods known to those skilled in the art.

Figure 8A:
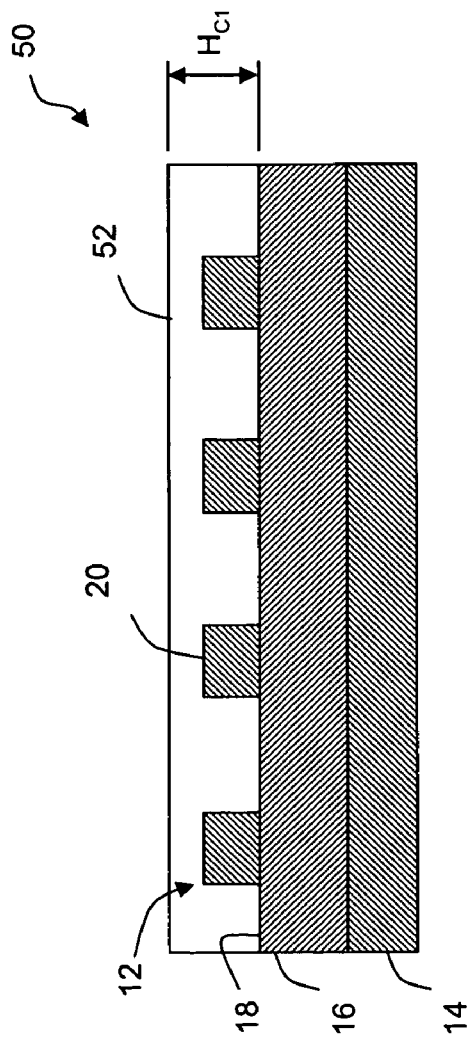
FIG. 8A shows a cross-sectional elevation view of an alternative embodiment of a wavelength selective surface having an over layer covering electrically conductive surface elements.

Referring to FIG. 8A a cross-sectional elevation view of an alternative embodiment of a wavelength selective surface 50 is shown having an over layer 52. Similar to the embodiments described above, the wavelength selective surface 50 includes an electrically conductive outer layer 12 having an arrangement of surface elements 20 (FIG. 1) disposed at a height above a ground layer 14 and separated therefrom by an intermediate layer 16. The over layer 52 represents a fourth layer, or superstrate 52 provided on top of the electrically conductive surface layer 12.

The over layer 52 can be formed having a thickness $H_{C1}$ measured from the intermediate layer surface 18. In some embodiments, the over layer thickness $H_{C1}$ is greater than thickness of the surface elements 20 (i.e., $H_{C1}>H_P$). The over layer 52 can be formed with varying thickness to provide a planar external surface. Alternatively or in addition, the over layer 52 can be formed with a uniform thickness, following a contour of the underlying electrically conductive surface 12.

An over layering material 52 can be chosen to have selected physical properties (e.g., k, n) that allow at least a portion of incident electromagnetic radiation to penetrate into the over layer 52 and react with one or more of the layers 12, 14, and 16 below. In some embodiments, the overlying material 52 is optically transparent in the vicinity of the primary absorption wavelength, to pass substantially all of the incident electromagnetic radiation. For example, the overlying material 52 can be formed from a glass, a ceramic, a polymer, or a semiconductor. The overlaying material 52 can be applied using any one or more of the fabrication techniques described above in relation to the other layers 12, 14, 16 in addition to painting and/or dipping.

In some embodiments, the over layer 52 provides a physical property chosen to enhance performance of the wavelength selective device in an intended application. For example, the overlaying material 52 may have one or more optical properties, such as absorption, refraction, and reflection. These properties can be used to advantageously modify incident electromagnetic radiation. Such modifications include focusing, de-focusing, and filtering. Filters can include low-pass, high-pass, band pass, and band stop.

The overlaying material 52 can be protective in nature allowing the wavelength selective surface 50 to function, while providing environmental protection. For example, the overlaying material 52 can protect the surface conductive layer 12 from corrosion and oxidation due to exposure to moisture. Alternatively or in addition, the overlaying material 52 can protect either of the exposed layers 12, 16 from erosion due to a harsh (e.g., caustic) environment. Such harsh environments might be encountered routinely when the wavelength selective surface is used in certain applications. At least one such application that would benefit from a protective overlaying material 52 would be a marine application, in which a protective over layer 52 would protect the electrically conductive layer 12 or 32 from corrosion.

Figure 8B:
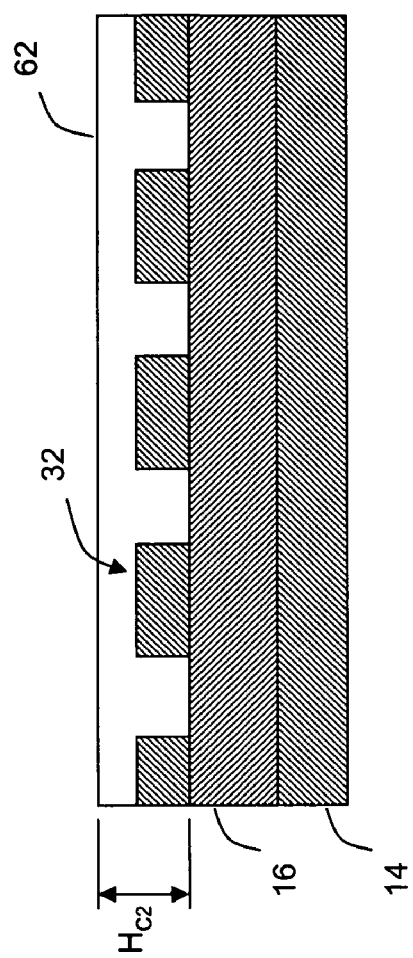
FIG. 8B shows a cross-sectional elevation view of an alternative embodiment of a wavelength selective surface having an over layer covering an electrically conductive surface layer and apertures defined therein.

In another embodiment shown in FIG. 8B, a wavelength selective surface 60 includes an overlying material 62 applied over a conductive layer 32 defining an arrangement of through apertures 34 (FIG. 6). The overlying material 62 can be applied with a maximum thickness $H_{C2}$ measured from the intermediate layer surface 18 to be greater than the thickness of the conductive layer 32 (i.e., $H_{C2}>H_P$). The overlaying material 62 again can provide a planar external surface or a contour surface. Accordingly, a wavelength selective surface 60 having apertures 34 defined in an electrically conductive layer 32 is covered by an overlying material 62. The performance and benefits of such a device are similar to those described above in relation to FIG. 8A.

Figure 9A:
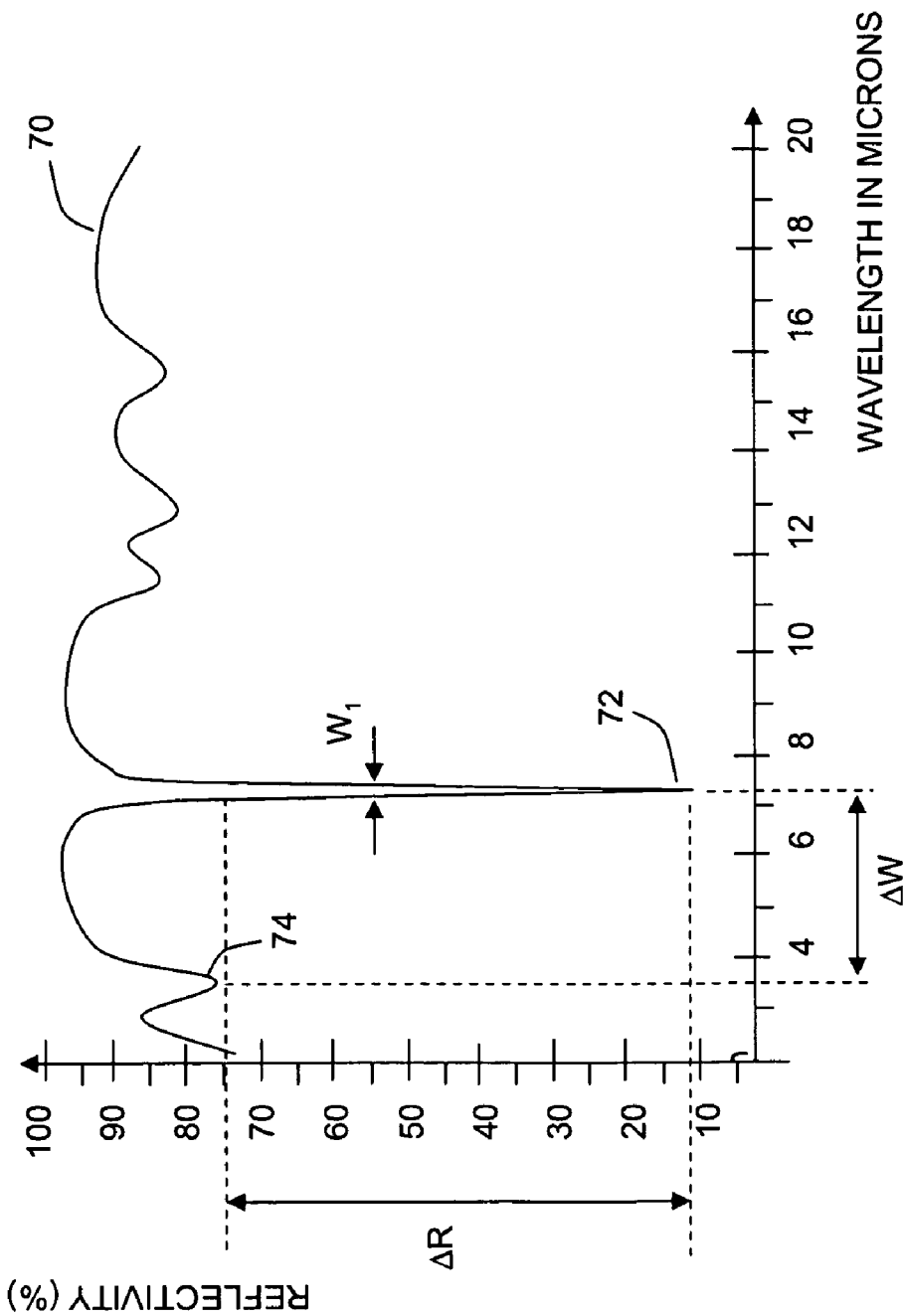
FIG. 9A shows in graphical form, an exemplary reflectivity-versus-wavelength response of a narrowband wavelength selective surface constructed in accordance with the principles of the present invention.

Referring to FIG. 9A, an exemplary reflectivity versus wavelength response curve 70 of a representative narrow-resonance response is shown in graphical form. The response curve 70 is achieved by exposing a wavelength selective surface 10 (FIG. 1) constructed in accordance with the principles of the present invention to incident electromagnetic radiation 22 (FIG. 1) within a band including a resonance. As shown, the reflectivity to incident electromagnetic radiation varies according to the curve 70 within the range of 0% to 100%. As the wavelength of the incident radiation 22 is varied from 2 to 20 microns, the reflectivity starts at a relatively high value of about 75%, increases to a value of over 85% at about 3 microns, reduces back to about 75% at about 3.5 microns, and increases again to nearly 100% between about 3.5 and 7 microns. Between 7 and 8 microns, the reflectivity response curve 70 incurs a second and more pronounced dip 72 to less then 20% reflectivity. The second dip 72 is steep and narrow, corresponding to absorption of incident electromagnetic radiation by the surface 10. The reflectivity response curve 70 at wavelengths beyond about 8 microns rises sharply back to more than 90% and remains above about 80% out to at least 20 microns. This range, from 2 to 20 microns, represents a portion of the electromagnetic spectrum including infrared radiation.

The second and much more pronounced dip 72 corresponds to a primary resonance of the underlying wavelength selective surface 10. As a result of this resonance, a substantial portion of the incident electromagnetic energy 22 is absorbed by the wavelength selective surface 10. A measure of the spectral width of the resonance response 70 can be determined as a width in terms of wavelength normalized to the resonant wavelength (i.e., $\Delta\lambda/\lambda_c$ or $d\lambda/\lambda_c$). Preferably, this width is determined at full-width-half-maximum (FWHM). For the exemplary curve, the width of the absorption band at FWHM is less than about 0.2 microns with an associated resonance frequency of about 7 microns. This results in a spectral width, or $d\lambda/\lambda_c$ of about 0.03. Generally, a $d\lambda/\lambda_c$ value of less than about 0.1 can be referred to as narrowband. Thus, the exemplary resonance is representative of a narrowband absorption response.

Results supported by both computational analysis of modeled structures and measurements suggest that the resonant wavelength associated with the primary resonance response 72 corresponds to a maximum dimension of the electrically conductive surface elements (e.g., a diameter of a circular patch D, or a side length of a square patch D'). As the diameter of the surface elements is increased, the wavelength of the primary absorption band 72 also increases. Conversely, as the diameter of the surface elements is decreased, the wavelength of the primary absorption band 72 also decreases.

The first, less pronounced dip 74 in reflectivity corresponds to a secondary absorption band of the underlying wavelength selective surface 10. Results supported by both computational analysis of modeled structures and measurements suggest that the wavelength associated with the secondary absorption band 74 corresponds at least in part to a center-to-center spacing of the multiple electrically conductive surface elements. As the spacing between surface elements 20 in the arrangement of surface elements 12 is reduced, the wavelength of the secondary absorption band 74 decreases. Conversely, as the spacing between the arrangement of surface elements 12 is increased, the wavelength of the secondary absorption band 74 increases. The secondary absorption band 74 is typically less pronounced than the primary absorption band 72 such that a change in reflectivity ΔR can be determined between the two absorption bands 74, 72. A difference in wavelength between the primary and secondary absorption bands 72, 74 is shown as ΔW.

In general, the performance may be scaled to different wavelengths according to the desired wavelength range of operation. Thus, by scaling the design parameters of any of the wavelength selective surfaces as described herein, resonant performance can be obtained within any desired region of the electromagnetic spectrum. Resonant wavelengths can range down to visible light and even beyond into the ultraviolet and X-ray. At the other end of the spectrum, the resonant wavelengths can range into the terahertz band (e.g., wavelengths between about 1 millimeter and 100 microns) and even up to radio frequency bands (e.g., wavelengths on the order of centimeters to meters). Operation at the shortest wavelengths will be limited by available fabrication techniques. Current techniques can easily achieve surface feature dimensions to the sub-micron level. It is conceivable that such surface features could be provided at the molecular level using currently available and emerging nanotechnologies. Examples of such techniques are readily found within the field of micro-mechanical-electrical systems (MEMS).

Figure 9B:
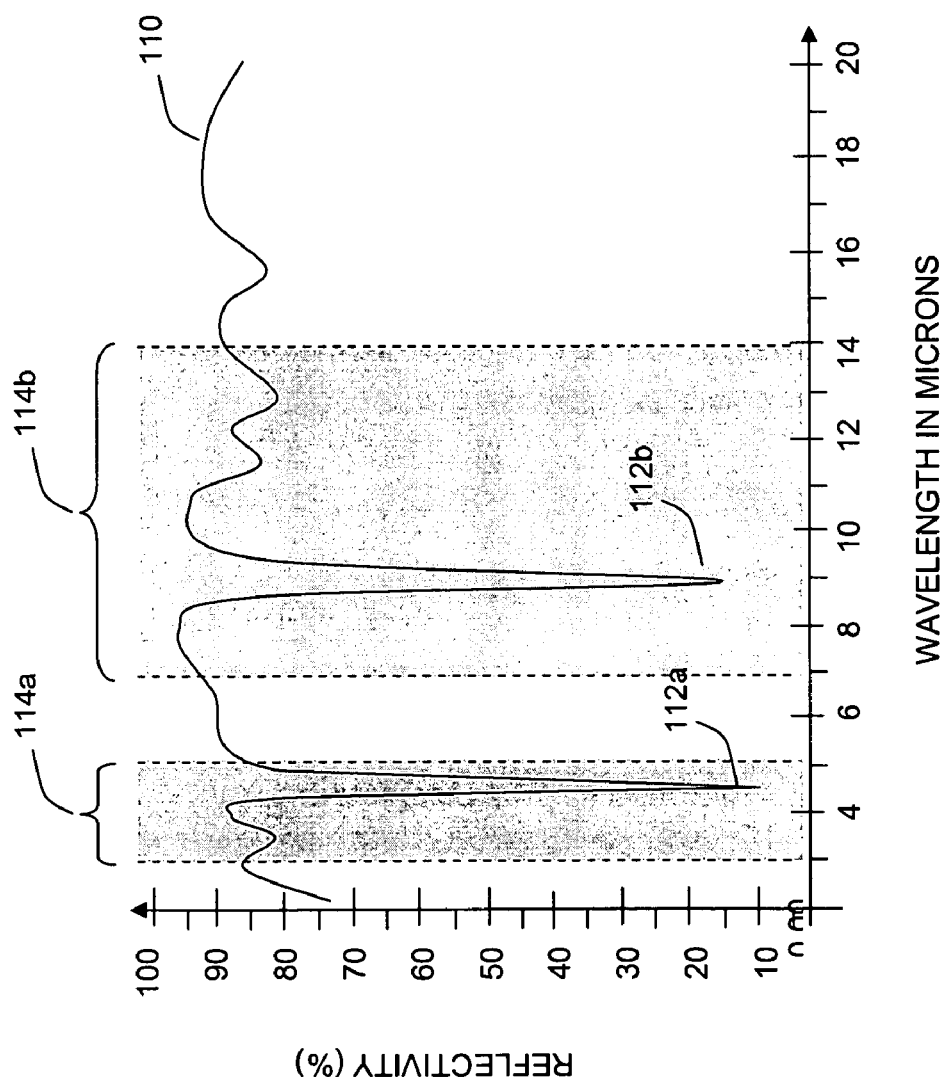
FIG. 9B shows in graphical form an exemplary reflectivity-versus-wavelength response of a dual resonance device constructed in accordance with the principles of the present invention.

An exemplary reflectivity versus wavelength response curve 110 is shown in FIG. 9B for a device 100 (FIG. 4) having more than one primary resonances. In this example, a first resonance 112a occurs at about 4.5 μm and a second resonance 112b occurs at about 9 μm. Also identified on the graph are two different channels within the IR band. A first channel 114a extends from about 3 μm to about 5 μm; whereas, the second channel 114b extends from about 7 μm to about 14 μm. Advantageously, the first resonance 112a resides within the first IR channel 114a and the second resonance 112b resides within the second IR channel 114b. In other embodiments of the present invention, one or more of the resonances 112a, 112b can be selected through the proper choice of design parameters, to reside at a wavelength outside of a channel 114a, 114b.

Figure 9C:
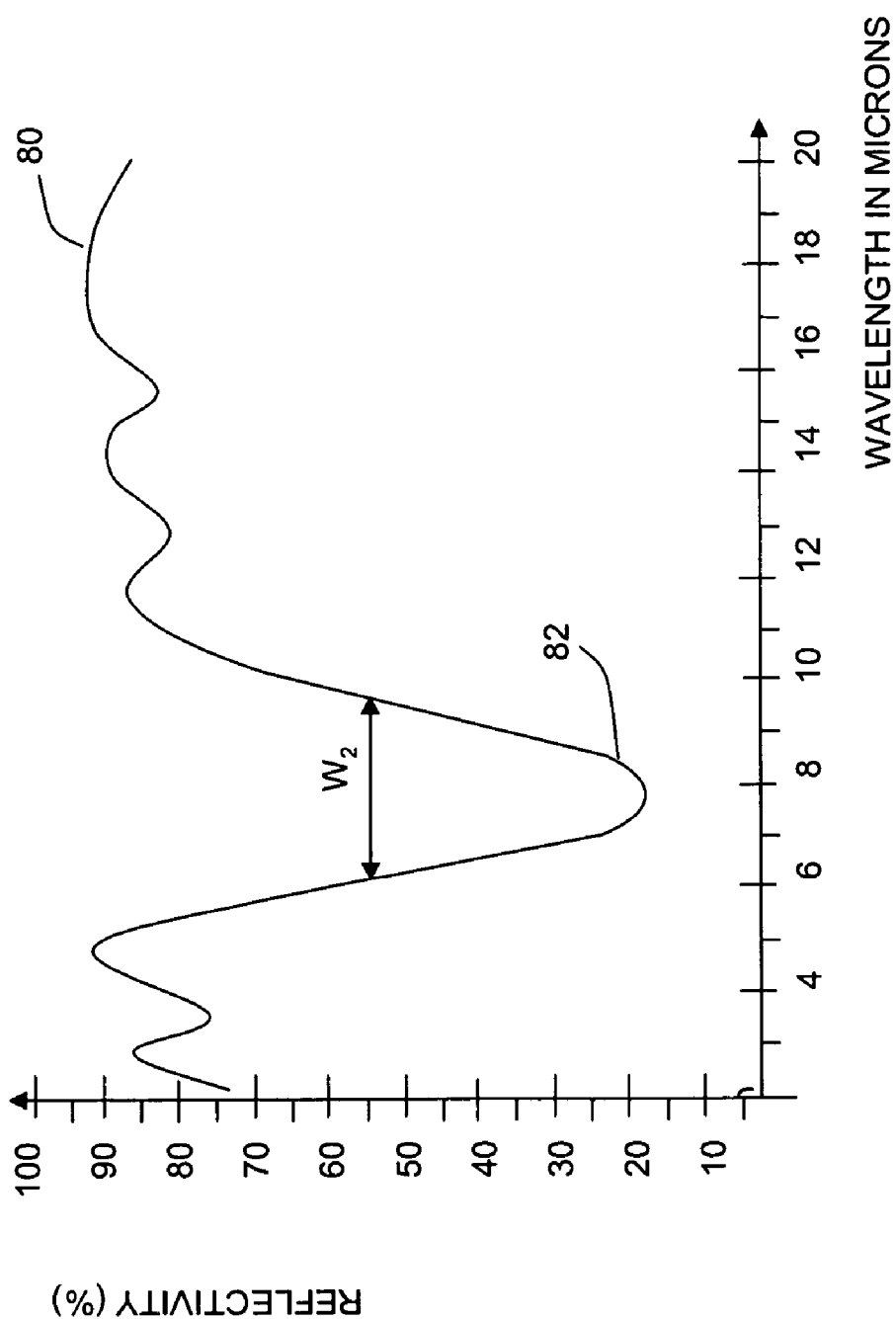
FIG. 9C shows in graphical form, an exemplary reflectivity-versus-wavelength response of a wideband wavelength selective surface constructed in accordance with the principles of the present invention.

Referring to FIG. 9C, an exemplary reflectivity versus wavelength response curve 80 of a wide-resonance wavelength selective surface is shown in graphical form. This wideband response curve 80 can also be achieved with the wavelength selective surface 10 (FIG. 1) constructed in accordance with the principles of the present invention, but having a different selection of design parameters. Here, a primary absorption band 82 occurs at about 8 microns, with wavelength range at FWHM of about 3 microns. This results in a spectral width $\Delta\lambda/\lambda_c$ of about 0.4. A spectral width value $\Delta\lambda/\lambda_c$ greater than 0.1 can be referred to as broadband. Thus, the underlying wavelength selective surface 10 can also be referred to as a broadband structure.

One or more of the physical parameters of the wavelength selective surface 10 can be varied to control reflectivity and absorption-emission response of a given wavelength selective surface. For example, the thickness of one or more layers (e.g., surface element thickness $H_p$, dielectric layer thickness $H_D$, and over layer thickness $H_C$) can be varied. Alternatively or in addition, one or more of the materials of each of the different layers can be varied. For example, the dielectric material can be substituted with another dielectric material having a different n and k values. The presence or absence of an over layer 52 (FIG. 8A), as well as the particular material selected for the over layer 52 can also be used to vary the reflectivity or absorption-emission response of the wavelength selective surface. Similar performance changes may be achieved by changing the material of the ground plane, change the dimension D of the surface elements, or by changing the shape of the surface elements.

In a first example, a wavelength selective surface includes an intermediate layer formed with various diameters of surface patches. The wavelength selective surface includes a triangular array of round aluminum patches placed over an aluminum film ground layer. The various surfaces are each formed with surface patches having a different respective diameter. A summary of results obtained for the different patch diameters is included in Table 1. In each of these exemplary embodiments, the patch spacing between adjacent patch elements was about 3.4 microns, and the thickness or depth of the individual patches and of the ground layer film were each about 0.1 micron. An intermediate, dielectric layer having thickness of about 0.2 microns was included between the two aluminum layers. It is worth noting that the overall thickness of the wavelength selective surface is about 0.4 microns—a very thin material. The exemplary dielectric has an index of refraction of about 3.4. Table 1 includes wavelength values associated with the resulting primary absorptions. As shown, the resonant wavelength increases with increasing patch size.

TABLE 1

Primary Absorption Wavelength Versus Patch Diameter

| Patch Diameter | Resonant Wavelength ($\lambda_c$) |
|---|---|
| 1.25 μm | 4.1 μm |
| 1.75 μm | 5.5 μm |
| 2.38 μm | 7.5 μm |
| 2.98 μm | 9.5 μm |

In another example, triangular arrays of circular patches having a uniform array spacing of 3.4 microns and patch diameter of 1.7 microns are used. A dielectric material provided between the outer conducting layers is varied. As a result, the wavelength of the primary absorption shifts. Results are included in Table 2.

TABLE 2

Resonance Versus Dielectric Material

| Dielectric material | Resonant Wavelength ($\lambda c$) |
|---|---|
| Oxide | 5.8 μm |
| Nitride | 6.8 μm |
| Silicon | 7.8 μm |

Figure 10:
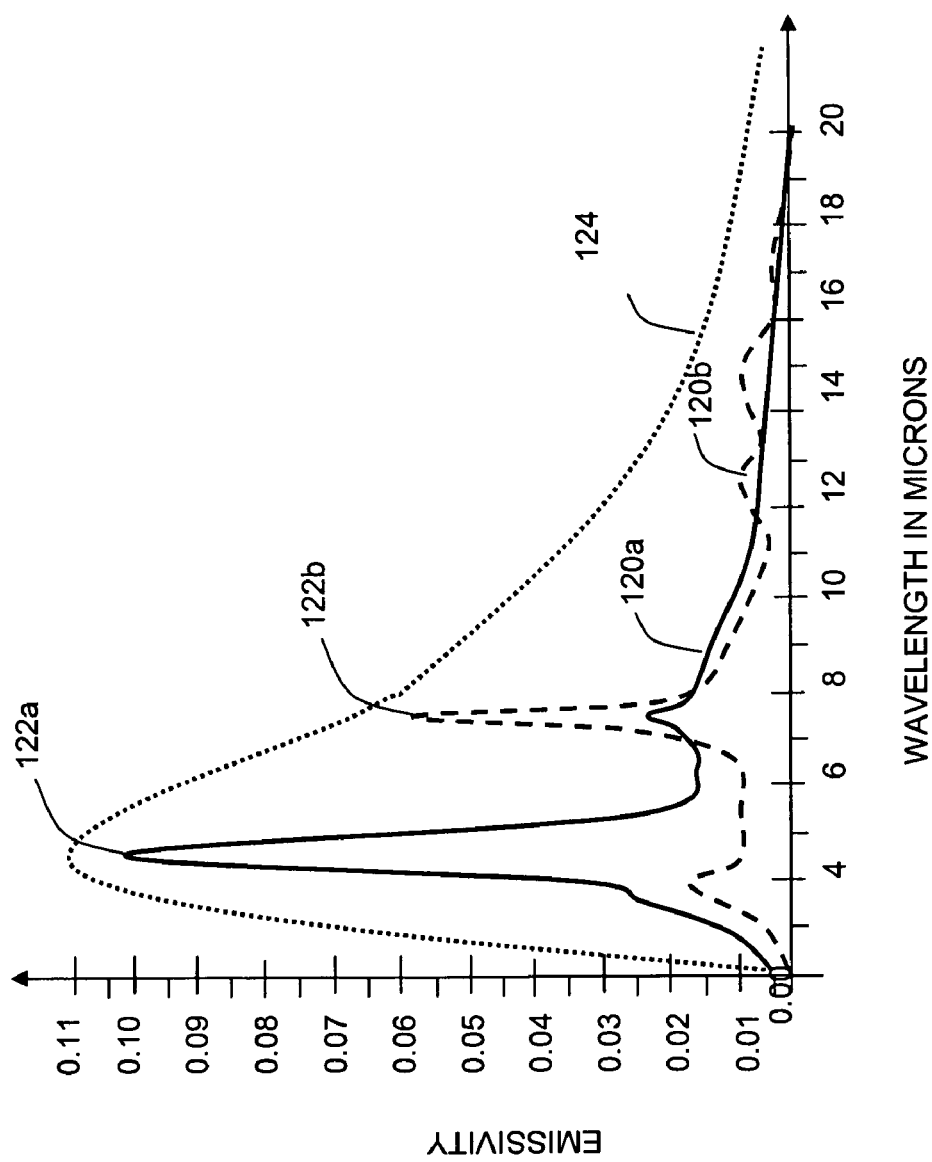
FIG. 10 shows in graphical form an exemplary emissivity-versus-wavelength response of different wavelength selective devices constructed in accordance with the principles of the present invention.

Referring to FIG. 10, an exemplary emissivity versus wavelength curve 120a is shown within a portion of the IR spectrum for a device fabricated in accordance with the present invention. When combined with a thermal source of radiation, wavelength selective surfaces according to the principles of the present invention produce a resonant response in emissivity as determined at least in part to one or more physical aspects of the underlying device.

As shown, the emissivity 120a is relatively low (e.g., below about 0.04) for wavelengths both below about 4 μm and above about 6 μm. However, at wavelengths between 4 μm and 6 μm a sharp rise in emissivity occurs producing a peak emissivity 122a corresponding to a resonant wavelength of the device. In the exemplary figure, the peak emissivity 122a is about 0.15 at a corresponding resonant frequency of about 4.5 μm. As with reflectivity, a measure of the resonant response can be defined by its selectivity determined as the spectral width at FWHM divided by the resonant frequency (i.e., $\lambda c/\lambda c$). A selectivity value of the first resonant peak is about 0.1, for narrowband operation.

Also shown is a second curve 120b having a different emissivity of about 0.06 at about 7.5 μm. Superimposed is a representative black body curve 124. Variation of one or more of the design parameters as described herein can be used to choose the resonant wavelength 122a, 122b. Thus, when the wavelength selective device or surface producing either curve 120a, 120b is applied to a thermal source, such as a filamentary heater, the emissivity of the blackbody thermal source is modified substantially to radiate only within a narrow band of wavelengths corresponding to resonance frequency. Thus, a narrowband (i.e., $\lambda c \lambda c < 0.1$) thermal source is possible combining the wavelength selective device with a broadband thermal radiation source to produce a substantially coherent IR source.

At least one important application for wavelength selective devices according to principles of the present invention is in gas detectors. As described in U.S. Pat. No. 7,119,337, incorporated herein by reference in its entirety, a narrowband thermal source can be tuned to an absorption band of a target gas. A sample of a substance, such as a gas is illuminated with the narrowband thermal source. A portion of the emitted spectrum is detected after propagating through the sample. When the target gas is present, the detected radiation will be substantially less due to absorption by the gas.

Figure 11:
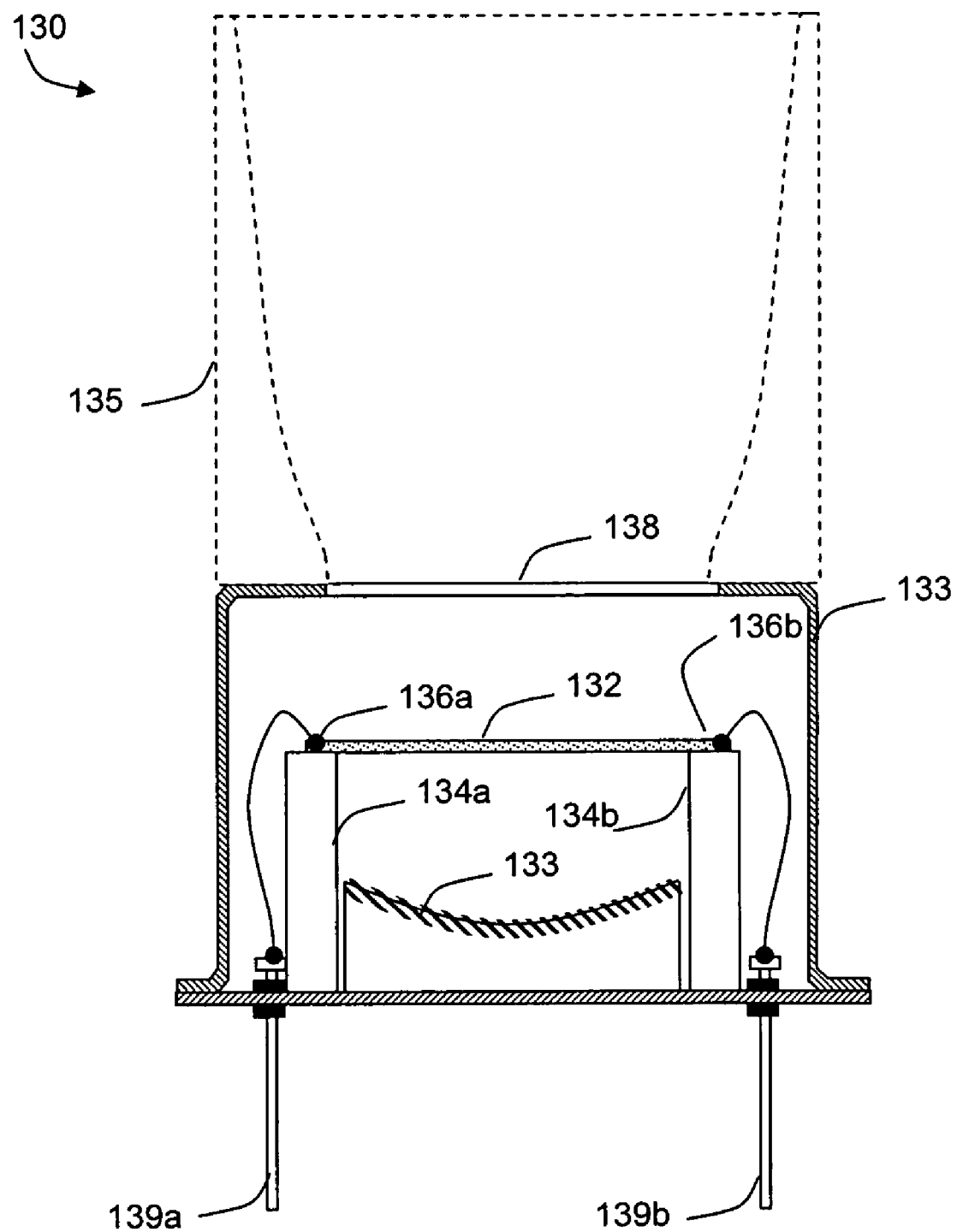
FIG. 11 is a cross-sectional elevation of an embodiment of the present invention packaged in a TO-8 windowed can.

Referring to FIG. 11, a thermal source 130 includes a narrowband IR source 132 within an electrical device package 134. In an exemplary embodiment, the IR source 132 is a horizontal thin film prepared in accordance with the device of FIG. 1, including an arrangement of uniform-sized electrically conductive surface patches above a ground plane separated by an intermediate thin-film layer of insulating material. The ground plane is provided with a finite conductivity having a real resistive component. The thin film device 132 is suspended in a bridge configuration between a pair of vertical support members 134a, 134b. Electrical terminals 136a, 136b are used to inject an electrical current into the ground plane of the emission device 132 to produce thermal energy through a process referred to as Joule heating, or equivalently as $I^2R$ heating.

The device package 133 may include a sealed housing, such as a TO-8 transistor used in standard process equipment, to isolate the IR source 132 from the environment. The package 133 includes at least one window 138 substantially aligned with an emission surface of the IR source 132, such that IR emissions can exit the package 133 to interact with the environment. The window 138 may include one or more optical properties including reflection, absorption, and transmission. In some embodiments, the device 130 includes a feature, such as the collar 135 shown providing a smooth reflective surface disposed around the IR source 132 and adapted to collect radiation emitted from the surface to selectively direct IR emissions within a preferred direction. Alternatively or in addition, a reflective member 133 is provided on the floor of the package, underneath the suspended IR source 132 (e.g., on an interior surface of the header of the transistor can shown) to reflect emission from a back side of the IR source 132 toward the window 138. Additionally, the package 133 includes one or more electrical leads 139a, 139b that can be used to inject an electrical current to drive the IR source 132. More generally, the IR source 132 includes any of the thin film wavelength selective surfaces described herein combined with a thin film thermal source—which can be the ground plane.

In some embodiments, a wavelength selective device, such as the IR source 132 above, includes additional layers, including a different respective insulating layer on each surface of the ground layer. Each insulating layer can have a respective arrangement of electrically conductive surface elements. Such a device is bidirectional in that it provides a respective reflectivity-absorption and emission profile on either side of the ground plane. A resonant performance of each of the different sides is independently controllable according to selected design parameters. In some embodiments, the design parameters of each side of the device are substantially identical yielding similar resonances. Alternatively, the design parameters of each side of the device are substantially different yielding different resonances.

Figure 12:
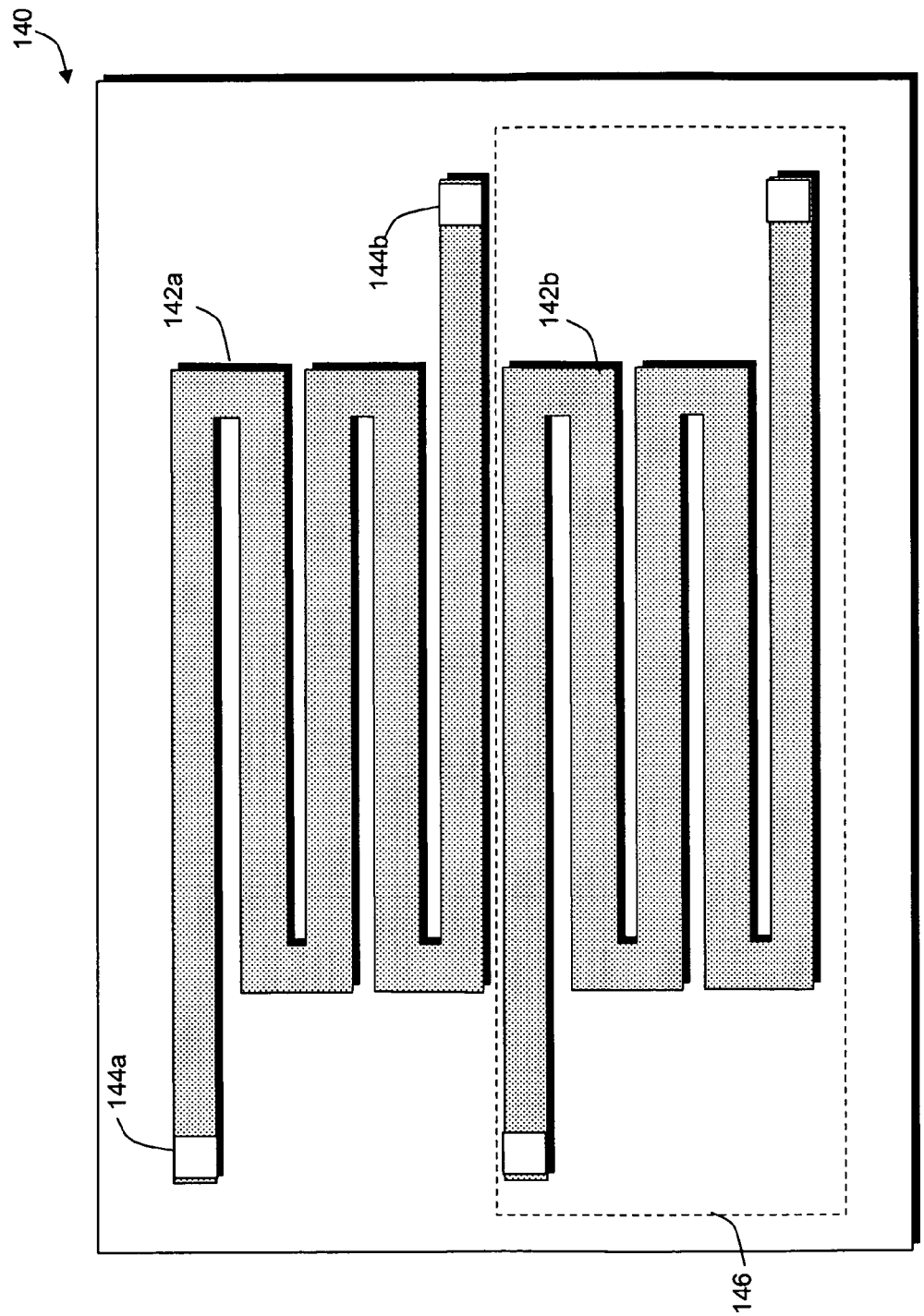
FIG. 12 is a plan view of an embodiment of the present invention formed in a serpentine ribbon.

Referring to FIG. 12, an IR source 140 can include a first IR source 142a formed in a ribbon or filament configuration. The first filament 142a can be formed in a serpentine shape, as shown, having electrical terminals 144a, 144b at either end. The electrical current can be applied between the terminals 144a, 144b causing a resistive ground plane to heat.

A second filament 142b can be provided within the same IR source 140. Preferably, the second filament 142b is constructed similar to the first 142a. In some embodiments, the second filament 142b is used as a detector, detecting a reflected return of IR emissions from the first filament 142a. In some embodiments, the second filament 142b is covered, or "blinded" by a screen 146. Thus, the second filament 142 shielded by the screen 146 does not respond to received IR from outside the package, but is allowed to respond to other environmental and device-dependent effects, such as ambient temperature and long-term variations in performance due to aging of the device. When formulated from the same material, the second filament 142b can be used as a reference to compare response measured on the first filament 142a. Thus, effects due to ambient temperature and long-term aging can be effectively removed from measurements obtained from the first.

In general, drive and readout schemes using a microprocessor controlled, temperature-stabilized driver can be used to determine resistance from drive current and drive voltage readings. That information shows that incidental resistance (temperature coefficient in leads and packages and shunt resistors, for instance) do not overwhelm the small resistance changes used as a measurement parameter.

Figure 13:
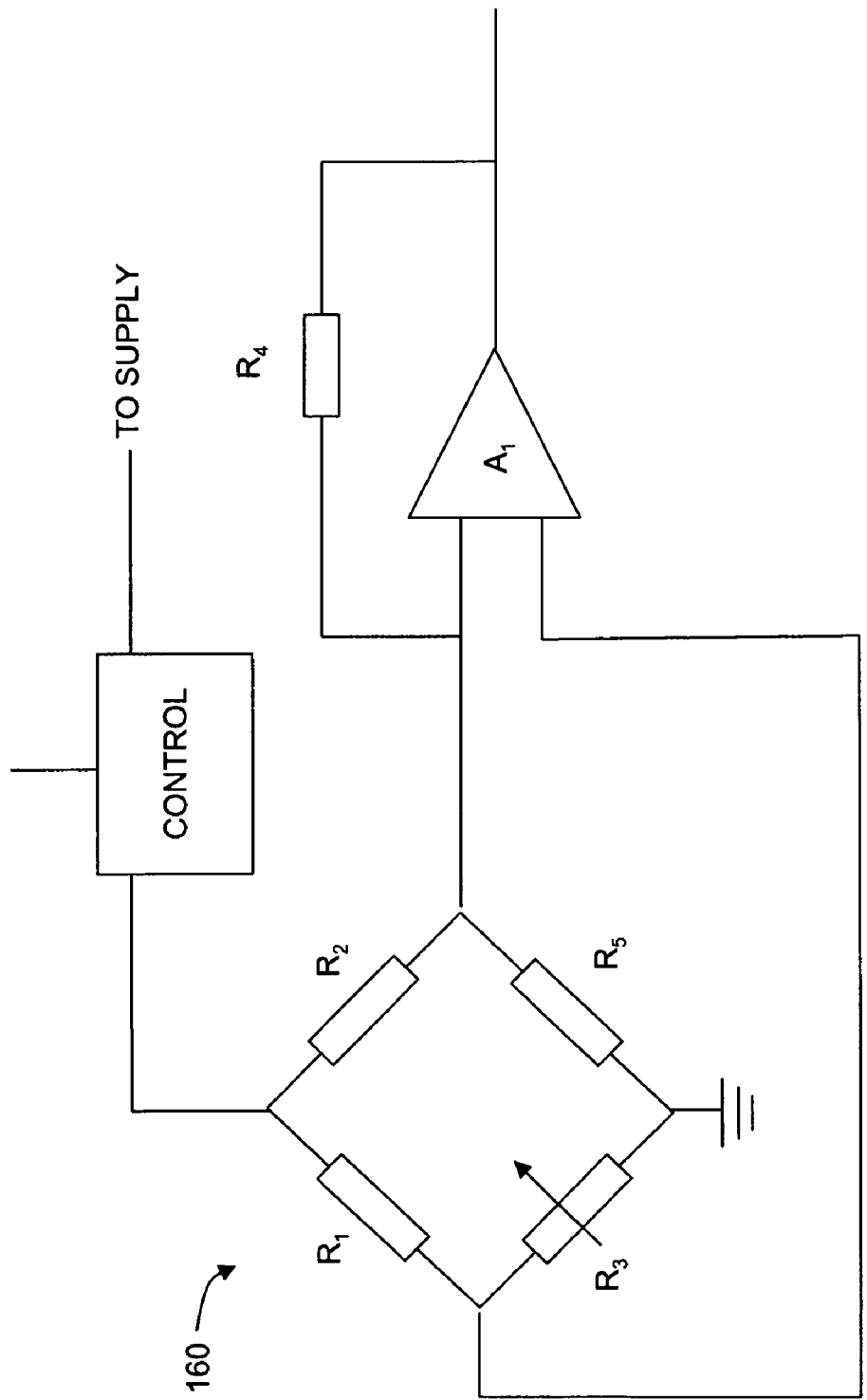
FIG. 13 is an exemplary bridge drive circuit for a wavelength selective surface constructed in accordance with the present invention.

For embodiments using a second detector for reference, the devices can be configured in a balanced bridge. Referring to FIG. 13, a Wheatstone bridge drive circuit 160 is shown. The Wheatstone bridge is a straightforward analog control circuit used to perform the function of measuring small resistance changes in a detector. It is very simple, very accurate, quite insensitive to power supply variations and relatively insensitive to temperature. The circuit is "resistor" programmable but depends for stability on matching the ratio of resistors. In one form, an adjacent "blind" detector element—an identical bolometer element filtered at some different waveband—is used as the resistor in the other leg of the bridge, allowing compensation for instrument and component temperatures and providing only a difference signal related to infrared absorption in the target gas.

In some embodiments, a wavelength selective emission device can be operated as both a source and a detector. For example, the emission device is heated using a thermal source, such as a resistive filament excited by an electrical current. The infrared radiation excites the arrangement of surface elements establishing a resonant coupling of the surface elements to other surface elements and to the ground plane. The result is an IR emission having a preferred spectra width (e.g., narrowband or wideband, depending upon the selection of design parameters). Heat is then removed from the source and the emission device is allowed to cool. The device can be used as a bolometer also detecting IR from an external environment or its own self-emission. The minimum duration of time between heating and cooling is limited by the thermal relaxation of the emission device. Preferably the thin film device is extremely thin, on the order of 10 μm or less, providing a very low thermal mass. Such thin film devices are capable of rapid cooling and can support thermal cycles approaching 1 to 2 Hz or even greater.

Figure 14A:
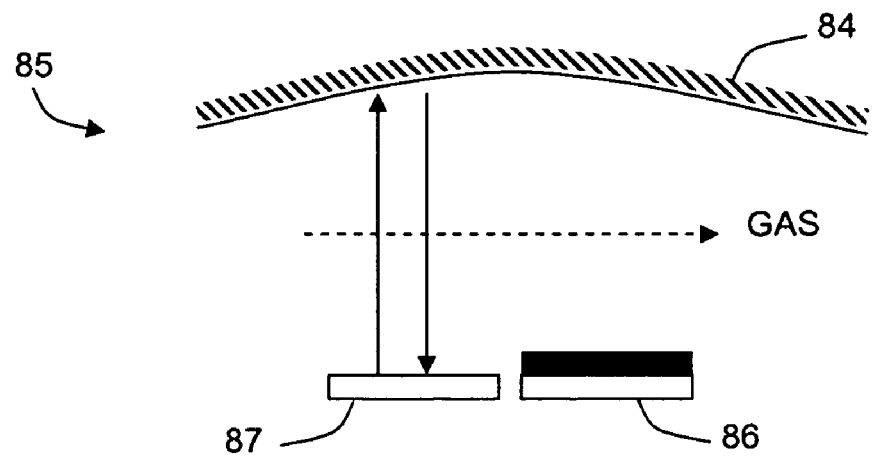
FIG. 14A shows in schematic form an embodiment of a substance detector including a single element source and detector with a spherical mirror.

Referring to FIG. 14A, one embodiment of a target material detector 85 provides an IR source including wavelength selective emission device 87 as described herein. Thus, the emission device 87 emits IR radiation at a wavelength selected to coincide with an absorption band of a target material, such as a gas. The resonant emission device 87 is aligned to emit radiation toward a target material (e.g., a gas). A reflecting surface such as a retro-reflective mirror, or a spherical mirror 84, is positioned opposite the emission device 87 (e.g., at a radial center of the spherical mirror), leaving a channel therebetween to accommodate a sample of the gas to be inspected for presence of the target component. In operation, radiation emitted from the emission device 87 passes through the gas sample toward the mirror 84. That portion of emitted radiation not absorbed by the sample gas reflects off of the mirror 84 and travels back toward the emission device 87 traversing the sample gas once again. When configured to act as an absorber and a receiver, the emissive device 87 detects the amount of received energy at the resonant wavelength. The detected value can be compared to the emitted value to determine an absorption value indicative of the target gas.

When a wavelength selective surface having multiple resonances is used, each of the multiple resonances can be individually tuned to a respective one of more than one target components. Such a device 85 is capable of detecting a preferred combination of different target elements. When all of the two or more target elements are present, absorption of the multi-resonant emissions result in a minimum detected return, as all of the multiple resonant emissions will endure absorption. However, when one or more of the two or more target elements are absent from the mixture, at least one of the corresponding resonant radiation emissions will suffer little or no absorption yielding a non-minimum detected return.

In some embodiments, a second emission device 86 is provided in the vicinity of the first 87. The first emission device 87 is tuned to the gas, while the second emission device 86 is tuned to a different wavelength, chosen to be outside the absorption band of any target elements in the gas. The return from the second emission device 86 can be used to measure other effects, such as ambient temperature changes and long-term changes due to device degradation. Results from the second emission device 86 can be combined with results from the first device 87, using techniques described herein, to effectively remove these secondary effects.

Figure 14B:
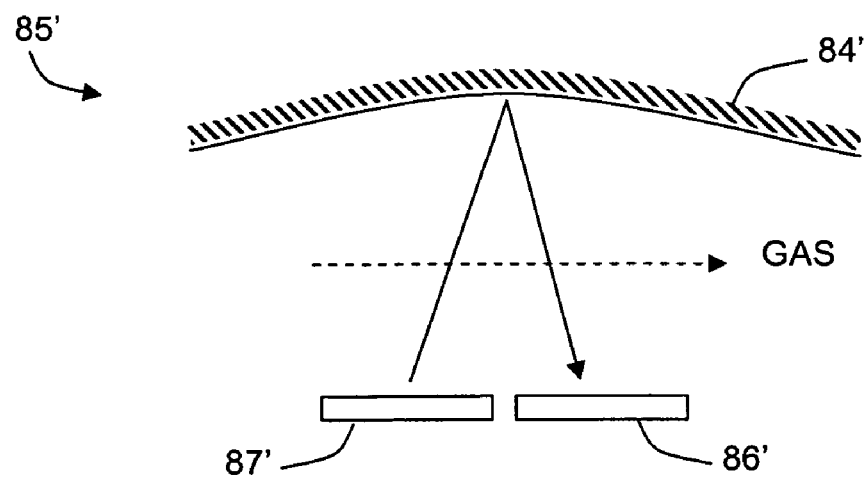
FIG. 14B shows in schematic form an alternative embodiment of a substance detector including separate source and detector elements using a reflective surface.

Referring to FIG. 14B, another embodiment of a reflective gas sensor 85' using a separate emission device 87' and detection device 86'. A mirror 84' is disposed within the optical path between the emission device 87' and the detection device 86'. The sample material is also disposed between the optical path, such that emitted radiation traverses the sample, such that absorption by a target element will bet evident by a reduced return at the detector 86'.

Figure 15A:
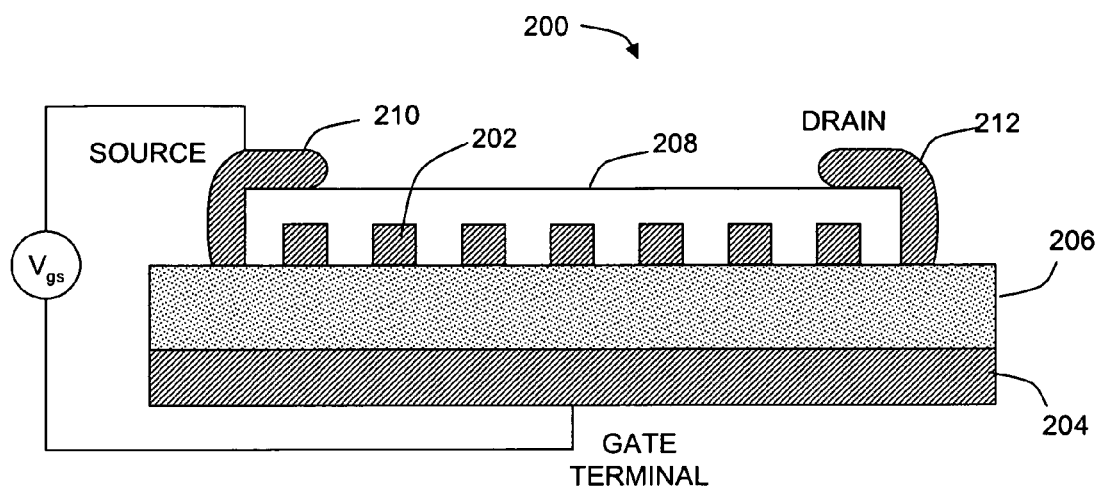
FIG. 15A is a side elevation of one embodiment of a wavelength selective surface having a controllable conductivity over layer.

In some embodiments, at least one of the layers of a wavelength selective device provides a controllable electrical conductivity. Preferably, the conductivity of the associated layer can be controlled using an external control mechanism to alter the resonant performance of the wavelength selective device. Referring now to FIG. 15A, a wavelength selective device 200 includes an arrangement of conductive surface elements 202 disposed above a ground layer 204. The conductive surface elements 202 are isolated from each other and separated from the ground layer 204 by an intermediate insulating layer 206. The wavelength selective device 200 provides a resonant response to incident electromagnetic radiation that depends on one or more of the design features of the device 200 as described herein. In the presence of electromagnetic radiation at wavelengths in and around the one or more resonant peaks, electromagnetic coupling fields are produced in and around the conductive surface elements 202 and particularly within the insulating layer 206 between each of the elements 202 and a localized region of the ground layer 204.

In the exemplary embodiment, an over layer 208 of insulating material covers the surface elements 202. In particular, the over layer 208 is made from a material having an electrical conductivity value that can be altered by an external control mechanism. When controlled to have a first conductivity that is substantially insulating, the device 200 demonstrates a resonant response to one or more of reflectivity, absorption, and emissivity. The first conductivity can be said to provide a relatively high impedance value that sufficiently maintains electrical isolation of the conductive surface elements 202. Upon activation by the external control mechanism, the over layer 208 provides a second conductivity value that is non-insulating, or electrically conducting. Being electrically conductive, or having a relatively low impedance value, the over layer 208 changes the resonant response of the device 200.

In some embodiments, the over layer 208 includes a semiconductor, such as silicon. The semiconductor itself behaves as an insulator. When doped with an appropriate element, the semiconductor can become electrically conductive in the presence of an applied electric field. Such techniques are well known to those skilled in the art of semiconductor fabrication. In order to provide an electric field to the semiconductor material, at least two terminals are provided: a source terminal 210 and a drain terminal 212. The intermediate insulating layer 206 can include an oxide, and the electrically conducting metal ground plane 204 can be used as a gate terminal, such that the device represents a metal-oxide-semiconductor (MOS) field effect transistor (FET). In particular, the structure represents a form of transistor referred to as a thin-film transistor (TFT).

Upon application of a sufficient gate-to-source voltage (Vgs), the electrical conductivity of the semiconductor over layer 208 changes from insulating (off) to conducting (on). Being electrically conducting, the surface elements 202 are short circuited together. Such a substantial change to the structure quenches the electromagnetic fields previously established between the surface elements 202 and the ground layer 204, thereby change the resonant response. When the surface elements 202 are shorted together in this manner, the resonant response essentially disappears, such that the wavelength selective device 200 can be selectively turned on and off as desired by controlling voltage signal applied between the gate and source terminals. This can be used to modulate the resonant response, be it reflectivity, absorption, and emissivity, at speeds (e.g., kilohertz through megahertz, and higher) much faster than would otherwise be possible considering the thermal relaxation response of the device. Thus, the resonant response is no longer limited by a thermal relaxation between cycles.

In other embodiments, the device 200 includes a similar architecture with an over layer 208 formed from an optically responsive material, such as photovoltaic material. Without illumination, or with insufficient illumination below some threshold value, the photovoltaic material 208 is substantially insulating allowing the device 200 to exhibit a resonant response according to the design parameters of the device 200. When illuminated sufficiently, the conductivity of the over layer 208 changes, becoming non-insulating, or electrically conductive. Such an increase in electrical conductivity substantially changes the resonant behavior of the device 200 by altering, and in some instances, electrically short-circuiting the arrangement surface elements 202. Thus, resonant performance of the device at one or more wavelengths of interest can be substantially modified by application of light energy at the same or different wavelengths. In such an embodiment, there would be no need for either a source terminal 210 or a drain terminal 212.

Figure 15B:
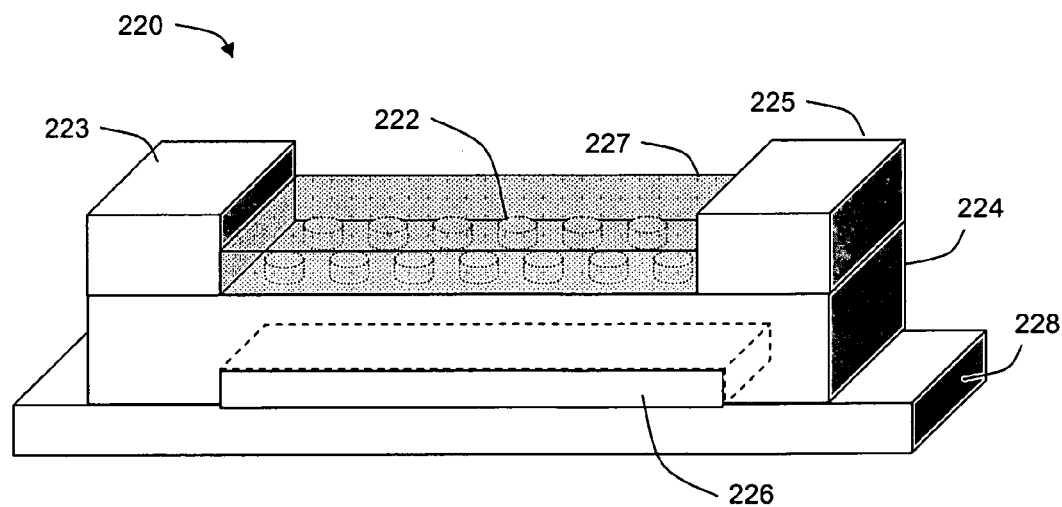
FIG. 15B is a top perspective diagram of an embodiment of a wavelength selective surface having a controllable conductivity over layer.

Referring to FIG. 15B, a top perspective view of one such device 220 is shown having an arrangement of surface elements 222 disposed on an insulating intermediate layer 224. A ground layer 226 is provided beneath the intermediate layer 224. An over layer 227 is applied over the arrangement of surface elements 222, having source terminal 223 and a drain terminal 225 disposed along opposite ends of the over layer 227. The entire device can be formed on a substrate 228. In some embodiments substrate 228 can be rigid, such as on a base Si wafer providing support to the transistor structure 220. In other embodiments, the substrate 228 can be flexible so that the device 220 can be contoured to the surface on which it is applied. At least one suitable flexible substrate includes polyimide films, commercially available from DuPont under the trade name KAPTON. Electrical contact can be made from an external source to one or more of the gate 226, source 223, and drain 225 terminals, such that application of an applied electrical signal can alter the conductivity of the over layer 227, thereby changing the resonant response of the wavelength selective device 220.

More generally, a similar approach can be used to controllably vary the conductivity of any one of the layers of a multi-layer wavelength selective device. In one embodiment, a ground plane layer can be included having a controllable conductivity. In some embodiments, the conductivity can be controlled by the application of an electrical signal. For example, the ground layer can include a suitably doped semiconductor material supporting an electrical current in the presence of an electric field above a threshold value. Thus, in the presence of a sufficient electric field, the ground layer becomes electrically conducting and the wavelength selective device operates according to the principals of the invention yielding a resonant response according to the chosen design parameters. However, upon variation of the electric field below the threshold, or its removal altogether, the ground layer becomes non-conducting, effectively removing the ground layer from the device. Such a substantial change in the configuration of the device quenches the standing wave electric fields in the dielectric and changes the overall reflection or absorption/emission resonance.

In another embodiment, the insulating layer includes a controllable conductivity. For example, the conductivity can be controlled by an electrical signal using a device such as a semiconductor for the insulating layer. Without application of a sufficient controlling electrical field, the insulating layer remains insulating allowing the wavelength selective device to operate according to the principals of the present invention yielding and providing a resonant response according to the chosen design parameters. However, upon the application of a sufficient electrical field, the insulating layer changes from insulating to non-insulating (or semi-insulating), thereby quenching the electromagnetic fields in the intermediate layer. Such a substantial change in the behavior of the ground layer alters the resonant performance, essentially turning the resonant performance off.

In addition to semiconductors, other materials can be used to provide a electrical conductivity controllable by an external control signal. Other examples include photovoltaic materials as described above and thermally responsive materials, such as pyroelectric materials that change conductivity in response to heat. Still other examples include chemically responsive materials, such as polymers that change conductivity in response to a local chemical environment. For example, the wavelength selective device includes an intermediate insulating layer formed from a photoconductor with a conductivity modified by incident light. Such a device would have an infrared reflection, and emission spectrum that could be modified by an external light source.

Alternatively or in addition, the intermediate layer includes a dielectric layer having an electrical conductivity that changes in response to its local chemical and/or physical environment. Such a device can serve as a remote sensor or tag for the relevant chemical or physical changes. Such a device can be remotely monitored through its infrared reflection/emission signature.

In yet other embodiments, the intermediate dielectric layer can have a conductivity or index of refraction that can be modified by a combination of the local environment and external illumination. One such example includes a fluorescent polymer.

Any of the above controllable devices can be used as an externally modulated, tuned electromagnetic emitter. This is particularly advantageous in the infrared band, wherein the device can be modulated rapidly, and faster than would otherwise be possible in view of thermal relaxation of the material.

Figure 16:
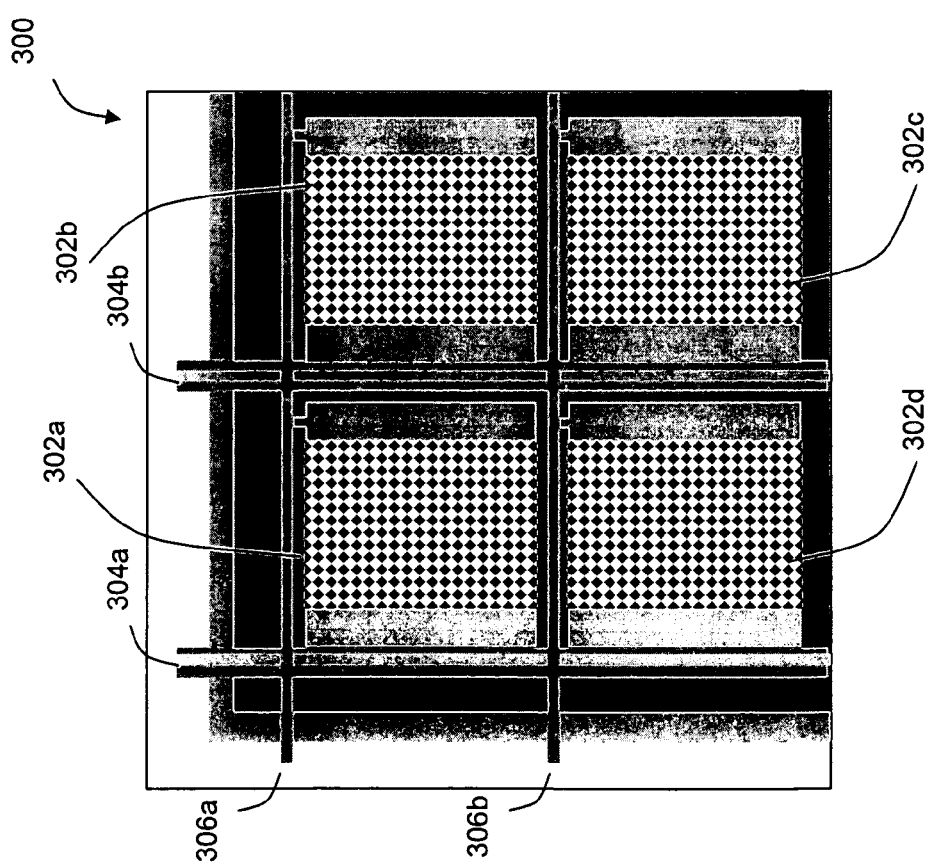
FIG. 16 is a plan view of an embodiment of a pixel incorporating wavelength selective devices.

A wavelength selective device that selectively reflects and/or emits electromagnetic radiation of a preferred wavelength can be used as a picture element, or pixel in a display device. Referring to FIG. 16, a pixel 300 is shown including a two-by-two rectangular matrix of sub-pixel elements 302a, 302b, 302c, 302d (generally 302). A pair of column electrodes 304a, 304b (generally 304) is aligned vertically, with each column electrode 304 connected to both sub-pixels 203 in its respective column. Likewise, a pair of row electrodes 306a, 306b (generally 306) is aligned horizontally, with each row electrode 306 connected to both sub-pixels 203 in its respective row. In particular, each of the sub-pixels can be individually addressed by applying a signal to the singular combination of column and row electrodes 304, 306 interconnected to the addressed sub-pixel 302. The pixel 300 can be formed on a substrate using techniques known to those skilled in the art of thin film displays, in which the film pixel elements include a resonant reflectivity and/or emissivity response as described herein.

Figure 17:
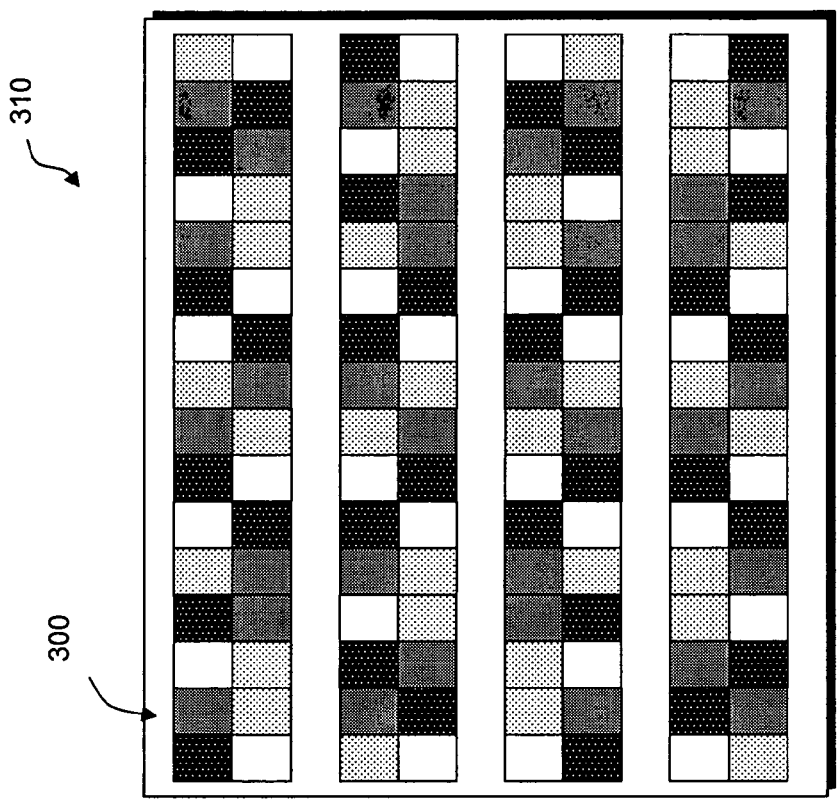
FIG. 17 is a schematic plan view of a matrix display incorporating the pixels of FIG. 16.

A schematic representation of a matrix display is shown in FIG. 17, using an array of pixel 300 elements according to principles of the present invention. In some embodiments, each of the sub-pixels 302 provides a resonant response at a substantially equivalent wavelength, or at least within the same band (e.g., the same IR band). In some embodiments, the intensity of the reflective response can be varied according to an applied control signal of each sub pixel 302. Such variation can be used to vary the intensity of a reflectivity dip (absorption spike) without substantially changing its resonant wavelength. For emissivity applications, such variation of a control input can be used to vary the intensity of emission spike, without substantially changing its resonant wavelength. With variations in intensity, the display 310 can be compared to a black and white visual display, having an array of pixels each displaying a controllable shade of gray (i.e., intensity).

In other embodiments, the pixel 300 includes an array of sub-pixels 302 in which each sub-pixel is tuned to a different respective wavelength. Thus, alternatively or in addition to the ability to control intensity of each of the sub pixels 302 as described above, each of the sub-pixels 302 can be actuated to provide a variable intensity, variable wavelength response. With variations in intensity and wavelength, the display 310 can be compared to a color visual display, having an array of pixels each including an array of sub-pixels to display different colors and intensity.

Thus, a complex picture can be formed within a portion of the electromagnetic spectrum determined by the resonant wavelength (e.g., IR), using a matrix display formed from a matrix of wavelength selective device as described using the principles described herein. The matrix display 310 can operate in a reflection mode, in which the display 310 is illuminated by an external electromagnetic radiation (e.g., an external IR source). A detector receiving reflections from the matrix display 310 captures a two-dimensional image formed thereon by selective activation of the individual pixels 300 of the array 310.

Alternatively or in addition, the matrix display 310 can operate in an emission mode, in which the display 310 emits electromagnetic radiation (e.g., IR). A detector, without the need of an external IR source, receives emissions from the matrix display 310, capturing an image formed thereon through selective activation of the individual pixels 300 of the array 310.

While this invention has been particularly shown and described with references to preferred embodiments thereof, it will be understood by those skilled in the art that various changes in form and details may be made therein without departing from the scope of the invention encompassed by the appended claims.

What is claimed is:

1. A tunable device for selectively coupling electromagnetic radiation comprising:
    a first electrically conductive layer including a plurality of discrete surface elements formed on or in the layer;
    an electrically insulating intermediate layer defining a first surface in communication with the electrically conductive surface layer;
    a second, continuous electrically conductive layer in communication with a second surface of the electrically insulating intermediate layer; and
    an electrode in electrical communication with at least one of the first electrically conductive layer, the electrically insulating intermediate layer, and the second continuous, electrically conductive layer, the plurality of discrete surface elements resonantly coupling at least a portion of the electromagnetic radiation with respect to the continuous electrically conductive layer;
    wherein the first electrically conductive layer, the electrically insulating intermediate layer, and the second continuous, electrically conductive layer form a wavelength selective element having at least one reflection or absorption-emission band; and
    wherein the wavelength selective element comprises a material having a material property that is variable in response to an external signal applied to the device, and wherein variation of the material property tunes the at least one reflection or absorption-emission band.

2. The device of claim 1, wherein the plurality of discrete surface elements comprises an array of uniform-sized electrically conductive elements.

3. The device of claim 2, wherein the uniformly shaped elements are selected from the group consisting of: closed curves; ellipses; circles; rectangles; squares; polygons; triangles; hexagons; parallelograms; stars having at least three legs; annular structures; and combinations thereof.

4. The device of claim 1, wherein the plurality of discrete surface elements are arranged in an array.

5. The device of claim 4, wherein the array is selected from the group consisting of: rectangular grids; square grids; triangular grids; Archimedean grids; and random arrangements.

6. The device of claim 1, wherein at least one of the first and second electrically conductive layers is formed from a metal.

7. The device of claim 1, wherein the electrically insulating intermediate layer comprises a dielectric material.

8. The device of claim 1, wherein at least one of the first electrically conductive layer, the electrically insulating intermediate layer, and the second continuous electrically conductive layer comprises a semiconductor.

9. The device of claim 1, wherein the plurality of discrete surface elements of the first electrically conductive layer comprises a plurality of through holes defined in an electrically conductive surface layer.

10. The device of claim 9, wherein the plurality of discrete through holes comprises an array of uniform-sized elements.

11. The device of claim 1, wherein the second, continuous electrically conductive layer comprises an electrically activated thermal source in communication with the electrode, the electrode receiving an electrical input to activate the thermal source.

12. The device of claim 1, wherein the second, continuous electrically conductive layer comprises a thermistor in thermal communication with the plurality of discrete surface elements and in communication with the electrode, the electrode enabling remote monitoring of the thermistor.

13. The device of claim 1, wherein two or more of the first electrically conductive layer, the electrically insulating intermediate layer, and the second continuous, electrically conductive layer are configured to provide a controllable switch, the electrode receiving an electrical input for controlling the switch.

14. The device of claim 1, wherein the external signal comprises at least one selected from the list consisting of: an electrical signal, a chemical signal, an optical signal, and a thermal signal.

15. The device of claim 1, wherein the material property comprises conductivity.

16. A tunable infrared emitter comprising:
a first electrically conductive layer including a plurality of discrete surface elements formed on or in the layer;
an electrically insulating intermediate layer defining a first surface in communication with the electrically conductive surface layer;
a second, continuous electrically conductive layer in communication with a second surface of the electrically insulating intermediate layer; and
an infrared source in thermal communication with at least one of the first electrically conductive layer, the electrically insulating layer and the second, continuous electrically conductive layer, the infrared source generating broadband infrared radiation, the plurality of discrete surface elements electromagnetically coupling at least a portion of the broadband infrared radiation,
wherein the first electrically conductive layer, the electrically insulating intermediate layer, and the second continuous, electrically conductive layer form a wavelength selective element having at least one infrared reflection or absorption-emission band; and
wherein the wavelength selective element comprises a material having a material property that is variable in response to an external signal applied to the device, and wherein variation of the material property tunes the at least one reflection or absorption-emission band; and
wherein the wavelength selective element interacts with the broadband infrared radiation to produce a narrowband infrared emission.

17. The device of claim 16, wherein tuned, narrowband infrared emission has a selectivity of not more than about 0.1, determined at a full-width-half-maximum spectral width.

18. The device of claim 16, wherein the infrared source comprises an electrical filament.

19. The device of claim 18, wherein the electrical filament includes the second, continuous electrically conductive layer.

20. The device of claim 16, wherein a total thickness of the first electrically conductive layer, the electrically insulating layer and the second, continuous electrically conductive layer is not more than about 10 μm.

21. The device of claim 20, wherein the device is suspended above a surface.

22. The device of claim 16, further comprising a thermistor in thermal communication with the plurality of discrete surface elements, the device selectively emitting infrared radiation in a tuned band determined by the electromagnetic coupling of the plurality of discrete surface elements.

23. The device of claim 16, wherein the external signal comprises at least one selected from the list consisting of: an electrical signal, a chemical signal, an optical signal, and a thermal signal.

24. The device of claim 16, wherein the material property comprises conductivity.

25. A controllable wavelength selective device, comprising:
a first electrically conductive layer including a plurality of discrete surface elements formed on or in the layer;
an electrically insulating intermediate layer defining a first surface in communication with the electrically conductive surface layer;
a second, continuous electrically conductive layer in communication with a second surface of the electrically insulating intermediate layer, wherein at least one of the first electrically conductive layer; the electrically insulating intermediate layer; and the second, continuous electrically conductive layer comprises a material having an electrical conductivity which is controlled in response to an external signal applied to the device;
wherein the first electrically conductive layer, the electrically insulating intermediate layer, and the second continuous, electrically conductive layer form a wavelength selective element having at least one reflection or absorption-emission band; and
wherein a property of the at least one reflection or absorption-emission band is controlled in response to the conductivity of the material.

26. The device of claim 25, wherein at least one of the first electrically conductive layer and the second, continuous electrically conductive layer comprises an electrical conductivity controllable between conducting and non-conducting, the controlled conductivity usable to control resonant performance of the device.

27. The device of claim 26, wherein at least one of the first electrically conductive layer and the second, continuous electrically conductive layer comprises a semiconductor material having a controllable electrical conductivity responsive to an electrical input.

28. The device of claim 26, wherein at least one of the first electrically conductive layer and the second, continuous electrically conductive layer comprises a pyroelectric material having a controllable electrical conductivity responsive to a thermal input.

29. The device of claim 25, wherein the electrically insulating intermediate layer comprises an electrical conductivity controllable between insulating and non-insulating, the controlled conductivity usable to control resonant performance of the device.

30. The device of claim 29, wherein the electrically insulating intermediate layer comprises a semiconductor material having a controllable electrical conductivity responsive to an electrical input.

31. The device of claim 29, wherein the electrically insulating intermediate layer comprises a pyroelectric material having a controllable electrical conductivity responsive to a thermal input.

32. The device of claim 29, wherein the electrically insulating intermediate layer comprises an optically responsive material having a controllable electrical conductivity responsive to an optical input.

33. The device of claim 29, wherein the electrically insulating intermediate layer comprises a chemically responsive material having a controllable electrical conductivity responsive to a change in a local chemical environment.

34. The device of claim 25, wherein the external signal comprises at least one selected from the list consisting of: an electrical signal, a chemical signal, an optical signal, and a thermal signal.

35. A method of manufacturing a wavelength selective device comprising:
   forming a continuous, electrically thin conductive ground layer on a substrate;
   applying an electrically thin insulating layer to a top surface of the ground layer;
   forming an electrically thin outer conductive layer on the electrically thin insulating layer,
   forming a plurality of discrete surface elements on or in the outer conductive layer;
   forming a wavelength selective element having at least one infrared reflection or absorption-emission band comprising the electrically thin conductive ground layer, the electrically thin insulating layer, and the electrically thin outer conductive layer; and
   wherein forming the wavelength selective surface comprises forming the wavelength selective surface to comprise a material having a material property that is variable in response to an external signal applied to the device, wherein variation of the material property tunes the at least one reflection or absorption-emission band.

36. The method of claim 35, wherein at least one of the layers is deposited using a thin film deposition technique.

37. The method of claim 35, wherein the discrete surface elements are formed using at least one of: laser ablation, removing selected regions of the conductive material from the surface; nano-imprinting; stamping; and standard semiconductor fabrication techniques.

38. The method of claim 35, wherein the substrate is flexible.

39. The method of claim 35, further comprising removing a sacrificial layer between a bottom surface of the ground layer and a substrate, removal of the sacrificial layer releasing a multi-layered thin-film device.

40. The method of claim 39, wherein the thickness of the multi-layered thin-film device is not more than about 10 μm.

41. The method of claim 35, wherein the external signal comprises at least one selected from the list consisting of: an electrical signal, a chemical signal, an optical signal, and a thermal signal.

42. The method of claim 35, wherein the material property comprises conductivity.

* * * * *